(12) United States Patent
Ernst et al.

(10) Patent No.: US 10,150,777 B2
(45) Date of Patent: Dec. 11, 2018

(54) PRODUCTION OF PYRIPYROPENES FROM DRY BIOMASS

(71) Applicant: BASF SE, Ludwigshafen (DE)

(72) Inventors: Burkhard Ernst, Hasede (DE); Manfred Ehresmann, Maxdorf (DE); Christopher Koradin, Gommersheim (DE); Andreas Pletsch, Limburgerhof (DE); Melanie Bonnekessel, Ludwigshafen (DE); Thomas Kaeding, Mannheim (DE); Karin Schein-Albrecht, Worms (DE); Stefanie Demming, Mannheim (DE); Franz Weber, Eppelheim (DE); Wolfgang Siegel, Limburgerhof (DE); Hartwig Schroeder, Nussloch (DE); Stephan Freyer, Neustadt (DE); Peter Oedman, Neustadt (DE)

(73) Assignee: BASF SE, Ludwigshafen (DE)

( * ) Notice: Subject to any disclaimer, the term of this patent is extended or adjusted under 35 U.S.C. 154(b) by 196 days.

(21) Appl. No.: 14/778,788

(22) PCT Filed: Mar. 3, 2014

(86) PCT No.: PCT/IB2014/059381
§ 371 (c)(1),
(2) Date: Sep. 21, 2015

(87) PCT Pub. No.: WO2014/155214
PCT Pub. Date: Oct. 2, 2014

(65) Prior Publication Data
US 2016/0046645 A1 Feb. 18, 2016

(30) Foreign Application Priority Data
Mar. 28, 2013 (EP) .................... 13161548

(51) Int. Cl.
*C07D 493/04* (2006.01)
*C12P 17/18* (2006.01)
*A01N 43/40* (2006.01)

(52) U.S. Cl.
CPC ........... *C07D 493/04* (2013.01); *A01N 43/40* (2013.01); *C12P 17/181* (2013.01)

(58) Field of Classification Search
None
See application file for complete search history.

(56) References Cited

U.S. PATENT DOCUMENTS

| | | |
|---|---|---|
| 5,422,257 A | 6/1995 | Ohleyer |
| 5,807,721 A | 9/1998 | Omura et al. |
| 2004/0147766 A1 | 7/2004 | Stadler et al. |
| 2006/0135564 A1 | 7/2006 | Kim et al. |

FOREIGN PATENT DOCUMENTS

| | | |
|---|---|---|
| CA | 2787829 | 8/2011 |
| CA | 2788058 | 8/2011 |
| EP | 1889540 | 2/2008 |
| EP | 2119361 | 11/2009 |
| EP | 2186815 | 5/2010 |
| EP | 2223599 | 9/2010 |
| EP | 2426124 | 3/2012 |
| JP | 1992360895 | 12/1992 |
| JP | H06505403 | 6/1994 |
| JP | 1994184158 | 7/1994 |
| JP | 1996239385 | 9/1996 |
| JP | 1996259569 | 10/1996 |
| JP | 2004526742 | 9/2004 |
| WO | WO 1994009147 | 4/1994 |
| WO | WO 2004060065 | 7/2004 |
| WO | WO 2006129714 | 12/2006 |
| WO | WO 201108155 | 9/2011 |
| WO | WO 2014111398 | 7/2014 |

OTHER PUBLICATIONS

Cooney "Solid-Liquid Separation: Filtration" 6 pages available online at https://ocw.mit.edu/courses/chemical-engineering/10-445-separation-processes-for-biochemical-products-summer-2005/lecture-notes/lecture_9.pdf on Nov 11, 2010 via Wayback Machine (Year: 2010).*
Hu et al. "Characterization of two cytochrome P450 monooxygenase genes of the pyripyropene biosynthetic gene cluster from Penicillium coprobium" The Journal of Antibiotics (2011) 64, 221-227 (Year: 2011).*
Kim et al. "GERI-BP002-A, Novel Inhibitor of Acyl-CoA: Cholesterol Acyltransferase Produced by Aspergil/us fumigatus F93" The Journal of Antibiotics, 1996, vol. 49 (1) pp. 31-36 (Year: 1996).*
Mazur et al. "The Effects of Spray-Drying on the Viability of Fungous Spores" J. bacteriol vol. 71, 1956, p. 257-266 (Year: 1956).*
Omura et la. "Pyripyropenes, Highly Potent Inhibitiors of Acyl-CoA: Cholesterol Acyltransferase Produced by Aspergillus fumigatus" The Journal of Antibiotics , Jul. 1993, vol. 46, No. 7, pp. 1168-1169.*
PCIB "Aspergillus fumigatus FO-1289" taken from PCIDB—PhytoChemical Interactions DB http://www.genome.jp/db/pcidb/kna_species/16290 accessed on Oct. 28, 2017.*

(Continued)

*Primary Examiner* — Thane Underdahl
(74) *Attorney, Agent, or Firm* — Brinks Gilson & Lione

(57) ABSTRACT

The invention pertains to processes to produce dry biomass of pyripyropene producer organisms, processes to obtain pyripyropenes from such dry biomass, as well as to processes to produce compounds of Formula III and/or Formula IV and/or Formula V from the pyripyropenes obtained from the dry biomass. The invention does further pertain to the dry biomass itself, as well as processes using said dry biomass to obtain pyripyropenes for the production of compounds of Formula III and/or Formula IV and/or Formula V, including processes using said dry biomass to obtain pyripyropenes or compounds of Formula III and/or Formula IV and/or Formula V in order to produce pest control compositions, in particular insecticides, comprising such compounds.

22 Claims, 2 Drawing Sheets

(56) References Cited

OTHER PUBLICATIONS

MBL: Mold & Bacteria Consulting Laboratories "Sampling for Airborne Aspergillus species" ttps://www.moldbacteria.com/mold/sampling-airborne-aspergillus-species.html on Oct. 28, 2017, 3 pgs.*
Choi et al., "*Penicillium griseofulvum* F1959, High-Production Strain of Pyripyropene A, Specific Inhibotr of Acyl-CoA: Cholesterol Acyltransferase 2," Journal of Microbiology and Biotechnology, vol. 18, No. 10, (2008), pp. 1663-1665.
Eamvijarn et al., "Secondary Metabolites from a Culture of the Fungus *Neosartorya pseudofischeri* and their *In Vitro* Cytostatic Activity in Human Cancer Cells," Planta Medica, vol. 78, (2012), pp. 1767-1776.
Extended European Search Report, issued in EP Application No. 13161548.6, dated Jul. 10, 2013.
International Preliminary Report on Patentability, issued in PCT/IB2014/059381, dated Sep. 29, 2015.
International Search Report, issued in PCT/IB2014/059381, dated Jun. 30, 2014.
Jeong et al., "GRRI-BP001 Compounds, New Inhibitors of Acyl-CoA: Cholesterol Acyltransferase from *Aspergillus fumigatus* F37 I.Production, Isolation, and Physico-chemical and Biological Properties," The Journal of Antibiotics, vol. 48, No. 8, (1995), pp. 751-756.
Obata et al., "Chemical Modification and Structure-Activity Relationships of Pyripyropenes; Potent, Bioavailable Inhibitor of Acyl-CoA: Cholesterol O-Acyltransferase (ACAT)," Bioorganic & Medicinal Chemistry Letters, vol. 5, No. 22, (1995), pp. 2683-2688.
Ohtawa et al., "Synthesis and Structure-Activity Relationship of Pyripyropene A Derivatives as Potent and Selective Acyl-CoA: Cholesterol Acyltransferase 2 (ACAT2) Inhibitors: Part 1," Bioorganic & Medicinal Chemistry Letters, vol. 23, (2013), pp. 1285-1287.
Shiomi et al., "Meroterpenoids with Various Biological Activity Produced by Fungi," Pure Appl. Chem., vol. 71, No. 6, (1999), pp. 1059-1064.
Tomoda et al., "Pyripyropenes, Novel ACAT Inhibitors Produced by *Aspergillus fumigatus*, IV. Structure Elucidation of Pyripyropenes M to R," The Journal of Antibiotics, vol. 49, No. 3, (1996), pp. 292-298.
Wang et al., "Aflavinines and Other Antiinsectan Metabolites from the Ascostromata of *Eupenicillium crustaceum* and Related Species," Applied and Environmental Microbiology, vol. 61, No. 12, (1995), pp. 4429-4435.
Search Report, issued in EP 14774843.8, dated Sep. 27, 2016.
Itoh et al., "Reconstitution of a Fungal Meroterpenoid Biosynthesis Reveals the Involvement of a Novel Family of Terpene Cyclases," Nature Chemistry, vol. 2, (2010), pp. 858-864.
Hayashi et al., "Pyripyropenes, Fungal Sesquiterpenes Conjugated with α-Pyrone and Pyridine Moieties, Exhibits Anti-angiogenic Activity against Human Umbilical Vein Endothelial Cells," Biol. Pharm. Bull., vol. 32, No. 7, (2009), pp. 1261-1265.
Masi et al., "Fischerindoline, a Pyrroloindole Sesquiterpenoid Isolated from *Neosartorya pseudofischeri*, with in vitro Growth Inhibitory Activity in Human Cancer Cell Lines," Tetrahedron, vol. 69, (2013), pp. 7466-7470.

* cited by examiner

PRODUCTION OF PYRIPYROPENES FROM DRY BIOMASS

This application is a National Stage application of International Application No. PCT/IB2014/059381, filed Mar. 3, 2014. This application also claims priority under 35 U.S.C. § 119 to European Patent Application No. 13161548.6, filed Mar. 28, 2013.

This application claims priority to EP 13161548.6 filed Mar. 28, 2013, which is incorporated herein by reference in their entirety.

FIELD OF THE INVENTION

The invention pertains to processes to produce dry biomass of pyripyropene producer organisms, processes to obtain pyripyropenes from such dry biomass, as well as to processes to produce compounds of Formula III and/or Formula IV and/or Formula V from the pyripyropenes obtained from the dry biomass. The invention does further pertain to the dry biomass itself, as well as processes using said dry biomass to obtain pyripyropenes for the production of compounds of Formula III and/or Formula IV and/or Formula V, including processes using said dry biomass to obtain pyripyropenes or compounds of Formula III and/or Formula IV and/or Formula V in order to produce pest control compositions, in particular insecticides, comprising such compounds.

BACKGROUND OF THE INVENTION

Pyripyropenes are a group naturally occurring compounds, which are produced as secondary metabolites by microorganisms and in particular by several filamentous fungi. This group of compounds have attracted attention, because they show very potent inhibition of Acyl-CoA cholesterol acyltransferase (ACAT) in rat liver microsomes (Journal of Antibiotics (1996), 49 (3), 292-298) and have insecticidal activity against several insects, for example, against *Helicoverpa armigera* larva (Applied and Environmental Microbiology (1995), 61 (12), 4429-4435), Diamondback moth larva (WO2004/060065), *Tenebrio molitor* (WO2004/060065) and aphids (WO2006/129714).

Up till now, the chemical synthesis of pyripyropenes remains quite difficult, so that a large proportion of pyripyropenes is still produced via fermentation of microorganisms. Microorganisms having the capacity to produce pyripyropenes are for instance *Penicillium coprobium* PF-1169 strain (Journal of Technical Disclosure No. 500997/2008), *Aspergillus fumigatus* IF0-1289 strain (Japanese Patent Laid-Open Publication No. 360895/1992), *Eupenicillium reticulosporum* NRRL-3446 strain (Applied and Environmental Microbiology (1995), 61 (12), 4429-4435), *Penicillium griseofulvum* F1959 strain (WO2004/060065), as well as, *Aspergillus fumigatus* FO1289 and its mutant *Aspergillus fumigatus* FO1289-2501. Quite often these microorganisms, e.g. *Aspergillus fumigatus* FO1289 and its mutant *Aspergillus fumigatus* FO1289-2501 produce not only one, but several different pyripyropenes which differ in structures of their side chains (Journal of Antibiotics (1996), 49 (3), 292-298). Research in the area of pyripyropenes have not only let to the identification of pyripyropene producing microorganisms and the identification of different kinds of naturally occurring pyripyropenes, but have also provided a phletora of derivatives of pyripyropenes produced via chemical modification of naturally occurring ones. Examples of these derivatives as well as their production processes are disclosed in EP1889540, EP2119361, EP2186815 and EP2426124.

Harvesting the full potential of this interesting group of natural compounds and their derivatives will require the use of effective large scale production methods of pyripyropenes. However, production of pyripyropenes via fermentation of microorganisms and their collection via extraction from the produced biomass still suffers of technical problems and high costs caused during handling and storage of the produced biomass and/or connected to the handling of large volumes during and after extraction of pyripyropenes from the biomass. Technical problems of particular importance are for example a lack of means for long term storage of the produced biomass and the occurrence of high filter resistances during extraction of pyripyropenes from large volumes of biomass.

The present invention results in part from the discovery that it is possible to isolate pyripyropenes from dry biomass without suffering a negative influence on the yield of extracted pyripyropenes in comparison to extractions from non dried material. While at the same time the production of dry biomass and its use for extraction of pyripyropenes dramatically enhanced stability during storage of the biomass, reduces the processed volumes, results in low filter resistance during extraction of pyripyropenes and leads to higher concentrations of pyripyropenes after extraction.

SUMMARY OF THE INVENTION

The invention includes a process to obtain at least one pyripyropene comprising the steps of
a) culturing a pyripyropene producer organism in a culture broth under culture conditions, in which at least one pyripyropene is produced,
b) producing dry biomass from at least a part of the biomass obtained in step a),
c) obtaining at least one pyripyropene from the dry biomass produced in step b).

This process may comprise a step, wherein the dry biomass produced in step b) is produced directly via spray drying of the culture broth comprising the biomass, or is produced via drying of wet biomass obtained from the culture broth.

The wet biomass may be obtained from the culture broth via
a) filtration and/or centrifugation, or
b) filtration and application of mechanical pressure, or
c) filtration and/or centrifugation and application of mechanical pressure.

The wet biomass may has further been
a) re-suspended in a re-suspension medium,
b) homogenized, may have
c) a glucose content of less than 5 g/l, may has
d) a water content between more than 15% to less than 90%, or may have
e) a combination of at least two of these features a) to d).

The process as described above may further comprise a step, wherein the dry biomass is produced by drying in a spray dryer, a paste mill dryer, a flash dryer, a fluid bed dryer, or a rotary dryer. Preferably, the dry biomass is produced by drying in a spray dryer or a paste mill dryer. The dry biomass produced and used in the processes described above, may be stored from about 5 hours, or up to several years, before the pyripyropene is obtained. Further, the dry biomass mentioned above has preferably a content of residual water of less than 10%. In one embodiment of the invention, the dry biomass consists to more than 80% of particles having a particle size between 0.01 mm to 5 mm.

Preferably, the dry matter produced and used in the processes described above comprises at least 95% of the pyripyropene produced during culturing of the pyripyropene producer organism, i.e. the amount of pyripyropene comprised in the wet biomass harvested from the culture broth after fermentation of the pyripyropene producer organism. Preferably the pyripyropene producer organism belongs to the genus *Penicillium, Eupenicillium,* or *Aspergillus,* even more preferred the pyripyropene producer organism is selected from the group consisting of *Penicillium coprobium, Penicillium griseofulvum, Eupenicillium reticulosporum* and *Aspergillus fumigatus.* Most preferred, the pyripyropene producer organism is *Penicillium coprobium.*

The processes described above usually comprises a step, in which the pyripyropene is obtained from the dry biomass via extraction, preferably via extraction with a solvent selected from the group of methanol, toluene and ethyl benzene, or is a mixture of at least two of them. In one embodiment of the invention, the processes described above comprise a step of extraction of at least one pyripyropene from the dry biomass and separation of the solvent used for extraction from the extracted biomass via filtration, wherein the filter resistance is preferably below $5*10^{13}$ mPas/m².

The processes as described above may also comprise a step to produce at least one compound of Formula III, Formula IV or Formula V, wherein at least one pyripyropene is obtaining via a process as described above, and is used to produce at least one compound of Formula III, Formula IV or Formula V. These processes may further comprise the step of obtaining or purifying the compound of Formula III, Formula IV or Formula V, which may further be used to produce a pest control composition, which is preferably an insecticide. A further embodiment of the invention is dry biomass of a pyripyropene producer organisms comprising at least one pyripyropene and having a water content of less than 10%, or having a particle size between 0.01 mm to 5 mm, or having a water content of less than 10% and a particle size between 0.01 mm to 5 mm. The dry biomass is preferably from a pyripyropene producer organisms selected from the group of *Penicillium coprobium, Penicillium griseofulvum, Eupenicillium reticulosporum* and *Aspergillus fumigatus,* even more preferred, the dry biomass is from *Penicillium coprobium.*

A further embodiment of the invention is a process to obtain at least one compound of Formula I, or to produce, at least one compound of Formula III, Formula IV or Formula V, from dry biomass of a pyripyropene producer organisms comprising at least one pyripyropene and having a water content of less than 10%, or having a particle size between 0.01 mm to 5 mm, or having a water content of less than 10% and a particle size between 0.01 mm to 5 mm. The dry biomass is preferably from a pyripyropene producer organisms selected from the group of *Penicillium coprobium, Penicillium griseofulvum, Eupenicillium reticulosporum* and *Aspergillus fumigatus,* even more preferred, the dry biomass is from *Penicillium coprobium.* Preferably, this process is a process in which a compound of Formula II is obtained. In further embodiment, the obtained compound of Formula II is used to produce at least one compound of Formula III, Formula IV or Formula V, preferably used to produce a compound of Formula V. The process might even include a further step, in which at least one compound of Formula III, Formula IV or Formula V, preferably a compound of Formula V being produced during the process, is further used to produce a pest control composition comprising at least one compound of Formula III, Formula IV or Formula V. Preferably the pest control composition is an insecticide.

The invention does further include the use of dry biomass of a pyripyropene producer organisms comprising at least one pyripyropene and having a water content of less than 10%, or having a particle size between 0.01 mm to 5 mm, or having a water content of less than 10% and a particle size between 0.01 mm to 5 mm, to obtain at least one compound of Formula I. The dry biomass is preferably from a pyripyropene producer organisms selected from the group of *Penicillium coprobium, Penicillium griseofulvum, Eupenicillium reticulosporum* and *Aspergillus fumigatus,* even more preferred, the dry biomass is from *Penicillium coprobium.* Preferably, the dry biomass is used to obtain a compound of Formula II.

Also comprised by the invention is the use of use of dry biomass of a pyripyropene producer organisms comprising at least one pyripyropene and having a water content of less than 10%, or having a particle size between 0.01 mm to 5 mm, or having a water content of less than 10% and a particle size between 0.01 mm to 5 mm, in a process to produce at least one compound of Formula III, Formula IV or Formula V. The dry biomass is preferably from a pyripyropene producer organisms selected from the group of *Penicillium coprobium, Penicillium griseofulvum, Eupenicillium reticulosporum* and *Aspergillus fumigatus,* even more preferred, the dry biomass is from *Penicillium coprobium.*

Figure 1:
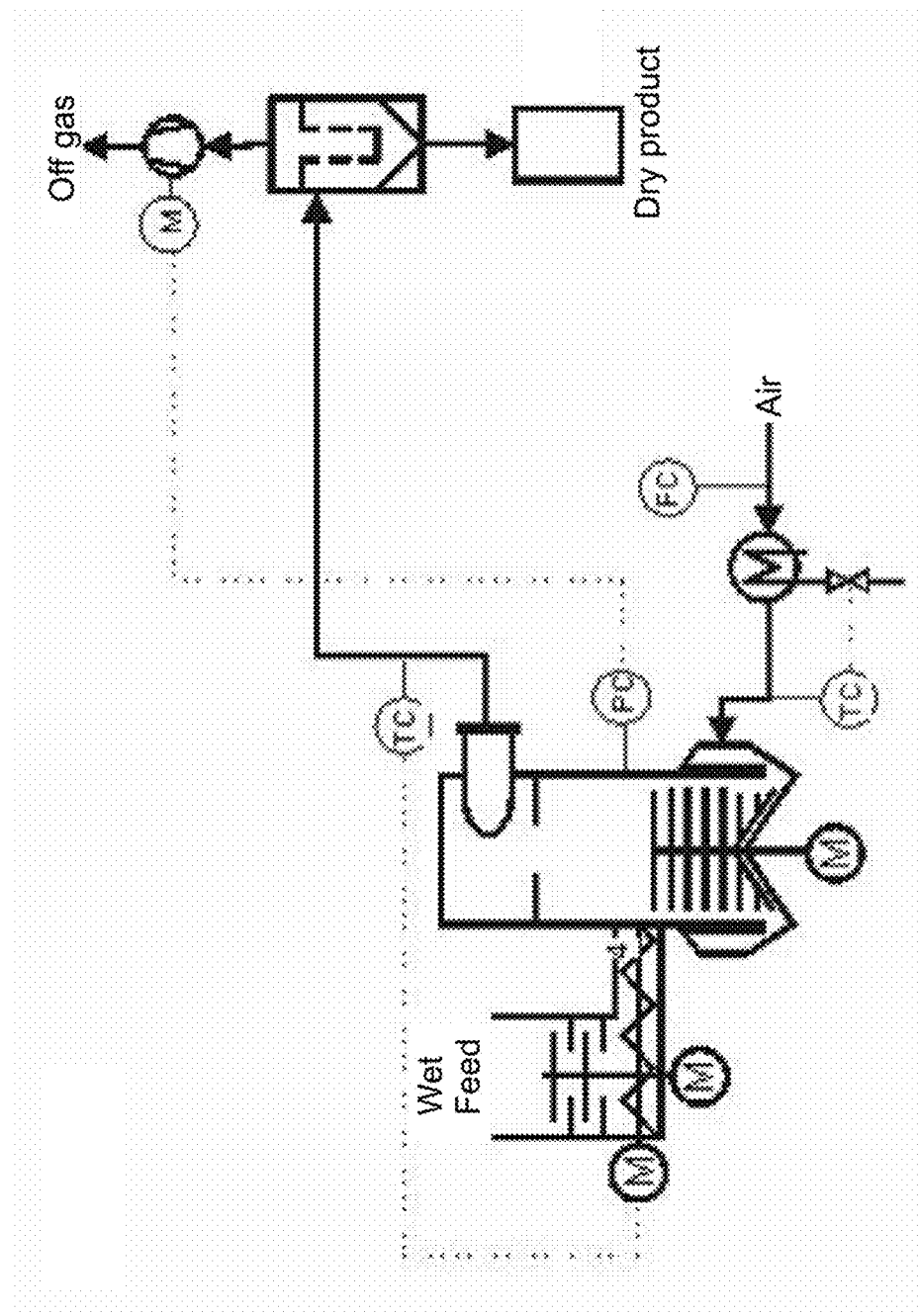
FIG. 1 depicts a schematic drawing of a paste mill dryer used in Examples I and II.

The process starts with a supply of wet biomass (Wet Feed) into a container on the left side of FIG. 1. The container is supplied with a rotor driven by a motor (M) at the bottom of the container, for homogenization of the wet biomass before it is fed to the paste mill dryer by a motor (M) powered screw. The paste mill dryer depicted on the left center side of FIG. 1, is again provided with a number of rotorknifes at the bottom third of the paste mill dryer. The rotorknifes are powered by a motor (M) at the bottom of the paste mill dryer. The paste mill dryer is also provided with a supply of hot air at the bottom third of its volume. The air flow is depicted on the lower right center of FIG. 1 and is characterized with a flow control (FC), a device for heating the air, and a temperature control (TC) which regulates the power of the heating device in order to provide the air with a predetermined inlet temperature. The hot air provided to the bottom third of the paste mill dryer mixes with the wet biomass provided by the srew and homogenized by the rotorknifes spinning close to the feed of the wet biomass. The result of this combination is that the wet biomass is taken up by a vortex of hot air into the middle third of the volume of the paste mill dryer, where it is dried. The dry biomass produced by this process is taken further up by the hot air into the head space (upper third of the volume) of the paste mill dryer, where it flows via a tube to a further container comprising a filter at the inside and being depicted on the right side of FIG. 1. The dry biomass is collected via the filter at the bottom of the container and can be emptied into a further container for storage or further transport of the dry biomass (Dry product). The tube connecting the paste mill dryer and the container comprising the funnel comprises a further sensor for temperature control (TC) which measures the temperature of the outgoing air stream (outlet temperature) and regulates the speed of the motor (M) driving the screw of the feed of wet biomass to the paste mill dryer. The paste mill dryer itself is provided further with a pressure control (PC) which controls a motor (M) located at the outlet of the container comprising the funnel and controlling the amount of air (Off gas) which can escape from the container comprising the funnel.

Figure 2:
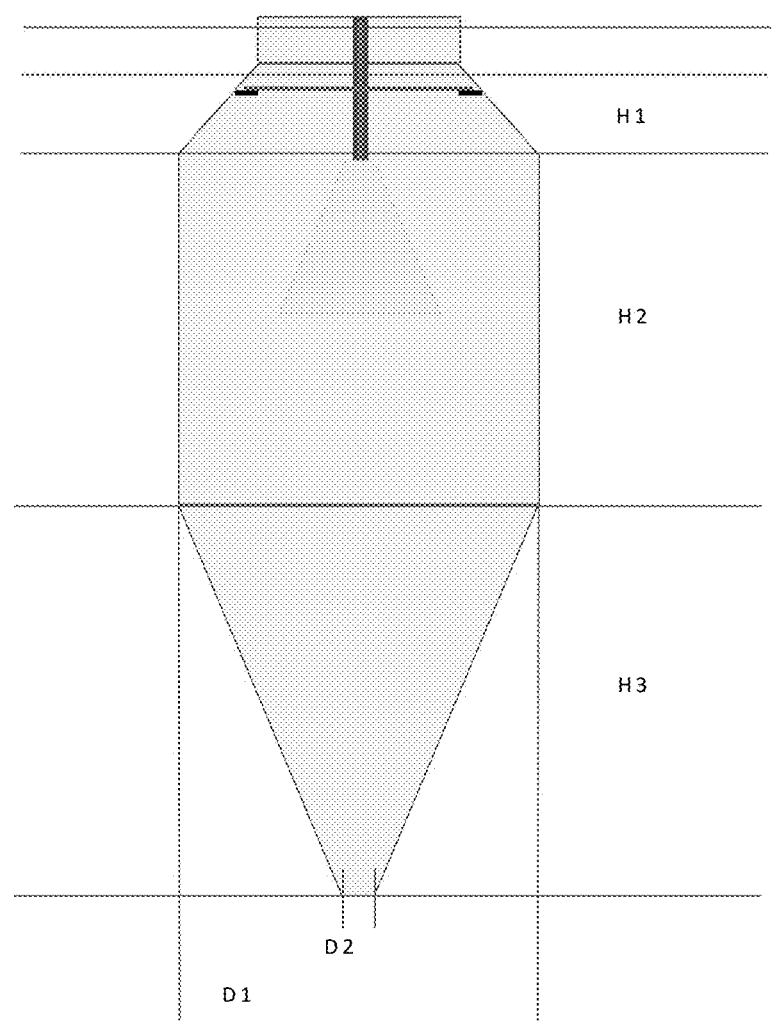

FIG. 2 depicts a schematic drawing of spray dryer used in Example III.

The spray dryer consists basically of a funnel like structure at the bottom of the spray dryer having a height described by H3, a total diameter at the upper part described by D1 and a diameter at the lower part or opening, respectively, described by D2. On top of this funnel like structure is a middle section formed as a barrel and having a height described by H2, and an upper and lower diameter identical to the upper diameter of the funnel like structure described by D1. The upper closed part of the spray dryer comprises a head space having a height described by H1. This head space comprises also a tube and a nozzle through which the wet biomass is fed and sprayed into the middle section of the spray dryer. The whole spray dryer is provided with a flow of hot air, which takes up the finely distributed wet biomass for drying in the co current flow down the dryer. A mixed flow of dried biomass and drying gas leaves the dryer at the bottom of the drier body towards a gas solid separator.

GENERAL DEFINITIONS

The terms "Pyripyropene" and "Pyripyropenes" means compound(s) of Formula I

For reasons of illustration, the term "Pyripyropene A" as described by Formula I and Table I means a compound of Formula II, which is also known as 1,7,11-tri-O-acetylpyripyropene A

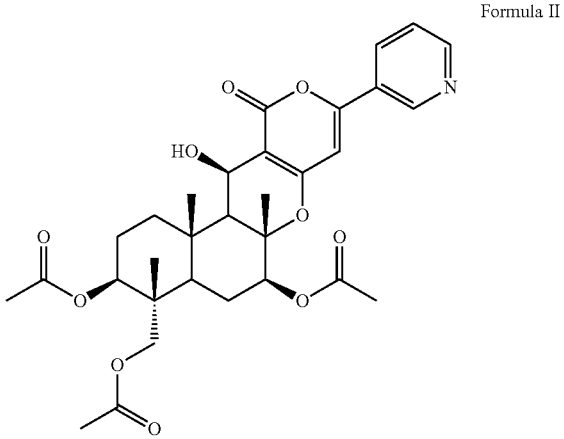

Formula II

Preferred pyripyropenes include pyripyropene A to pyripyropene O as described in Table 1, and are preferably pyripyropene A, E and O with pyripyropene A being the most preferred. Also preferred are compounds as described by Formula II, Formula III, Formula IV and Formula V.

The term "1,7,11-tri-deacetylpyripyropene A" means a compound of Formula III

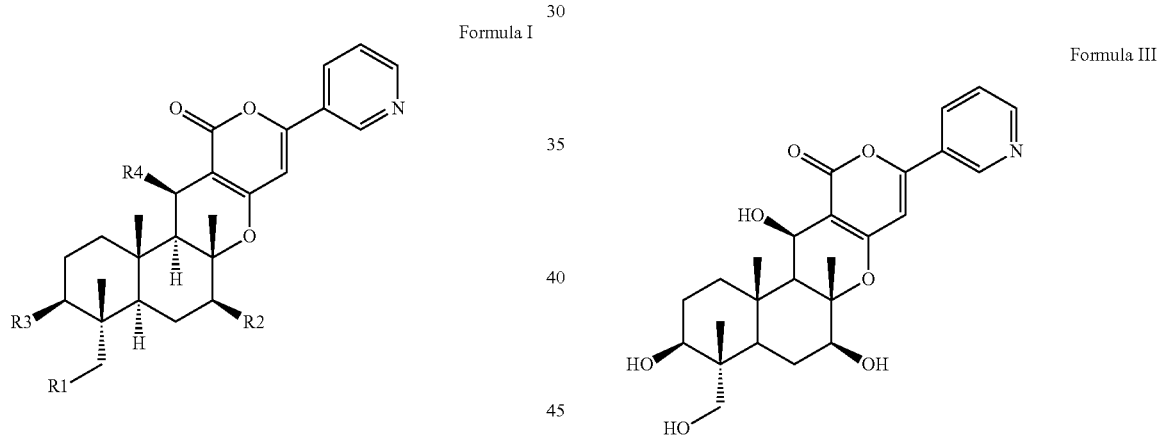

Formula I

Formula III wherein R1, R2, R3 and R4 have the combinations as depicted in Table 1

TABLE 1

Combinations of R1, R2, R3 and R4 of compounds of Formula I and names of compounds having such combinations

| Name | $R_1$ | $R_2$ | $R_3$ | $R_4$ |
| --- | --- | --- | --- | --- |
| Pyripyropene A | —OCOCH$_3$ | —OCOCH$_3$ | —OCOCH$_3$ | —OH |
| Pyripyropene B | —OCOCH$_2$CH$_3$ | —OCOCH$_3$ | —OCOCH$_3$ | —OH |
| Pyripyropene C | —OCOCH$_3$ | —OCOCH$_2$CH$_3$ | —OCOCH$_3$ | —OH |
| Pyripyropene D | —OCOCH$_3$ | —OCOCH$_3$ | —OCOCH$_2$CH$_3$ | —OH |
| Pyripyropene E | —H | —H | —OCOCH$_3$ | —H |
| Pyripyropene F | —H | —H | —OCOCH$_2$CH$_3$ | —H |
| Pyripyropene G | —H | —H | —OCOCH$_3$ | —OH |
| Pyripyropene H | —H | —H | —OCOCH$_2$CH$_3$ | —OH |
| Pyripyropene I | —OCOCH$_2$CH$_3$ | —OCOCH$_2$CH$_3$ | —OCOCH$_2$CH$_3$ | —OH |
| Pyripyropene J | —OCOCH$_3$ | —OCOCH$_2$CH$_3$ | —OCOCH$_2$CH$_3$ | —OH |
| Pyripyropene K | —OCOCH$_2$CH$_3$ | —OCOCH$_3$ | —OCOCH$_2$CH$_3$ | —OH |
| Pyripyropene L | —OCOCH$_2$CH$_3$ | —OCOCH$_2$CH$_3$ | —OCOCH$_3$ | —OH |
| Pyripyropene O | —OCOCH$_3$ | —H | —OCOCH$_3$ | —H |

The term "compound of Formula IV" means a compound of Formula I, wherein
R1 and R3 represent cyclopropylcarbonyloxy, and
R2 represents hydroxyl, cyclopropylcarbonyloxy, or 2-cyanobenzoyloxy
R4 represents hydroxyl,
Preferably the compound of Formula IV comprises a combination, wherein:
R1 represents hydroxyl,
R2 and R3 represent cyclopropylcarbonyloxy, and
R4 represents hydroxyl, or cyclopropylcarbonyloxy.

The term "1,11-di-O-cyclopropanecarbonyl-1,7,11-trideacetylpyripyropene A" means a compound of Formula V:

Formula V

Pyripyropenes described by Formula I, Formula II, Formula III, Formula IV and Formula V include also the salts of these compounds. Preferably the salts of the compounds of Formula I, Formula IV and Formula V. Examples of such salts include agriculturally or horticulturally acceptable acid addition salts such as hydrochloride salts, nitrate salts, sulfate salts, phosphoric salts, or acetate salts.

DETAILED DESCRIPTION OF PREFERRED EMBODIMENTS

The invention pertains to processes to produce dry biomass of pyripyropene producer organisms, processes to obtain pyripyropenes from such dry biomass, as well as to processes to produce compounds of Formula III and/or Formula IV and/or Formula V from the pyripyropenes obtained from the dry biomass.

The invention does further pertain to the dry biomass itself, as well as to the use of the dry biomass to obtain pyripyropenes or compounds of Formula III and/or Formula IV and/or Formula V and to the use of the dry biomass as insecticide or to produce an insecticide.

Accordingly, the invention comprises a process to obtain at least one pyripyropene comprising the steps of
a) culturing a pyripyropene producer organism in a culture broth under culture conditions, in which at least one Pyripyropene is produced,
b) producing dry biomass from at least part of the biomass obtained in step a),
c) obtaining at least one Pyripyropene from the dry biomass produced in step b).

The obtained pyropyropene can be used to produce derivatives of pyripyropene. Preferred derivatives of pyripyropene are compounds of Formula III, compounds of Formula IV and compounds of Formula V.

Thus, a further embodiment of the invention is a process to produce a derivative of pyripyropene, preferably a process to produce at least one compound of Formula III, Formula IV or Formula V, comprising:
a) obtaining pyripyropene from dry biomass comprising at least one pyripyropene,
b) producing at least one derivative of at least one pyripyropene from the pyripyropene obtained in step a), preferably producing at least one derivative of pyripyropene selected from the group of compounds consisting of the compound of Formula III, the compound of Formula IV and the compound of Formula V from the pyripyropene obtained in step a).

Another embodiment of the invention is a process to produce a derivative of pyrypyropene, preferably a process to produce at least one compound of Formula III, Formula IV or Formula V, preferably a compound of Formula V, comprising:
a) culturing a pyripyropene producer organism in a culture broth under culture conditions, in which at least one pyripyropene is produced,
b) producing dry biomass from at least part of the biomass obtained in step a),
c) obtaining at least one pyripyropene from the dry biomass produced in step b),
d) producing at least one derivative of at least one pyripyropene from the pyripyropene obtained in step c), preferably producing at least one derivative of pyripyropene selected from the group of compounds consisting of the compound of Formula III, the compound of Formula IV and the compound of Formula V from the pyripyropene obtained in step c).

The pyripyropene obtained in the processes described above is preferably obtained from the dry biomass via extraction according to methods available in the art, for example by the methods described further below.

The obtained pyripyropene, can either be purified by methods available in the art e.g. to produce the respective pyripyropene as a 90%, 95%, 96%, 97%, 98%, 99%, or close to 100% pure compound, or can be used, while still comprised in the solvent or solvents, for extraction for a process to produce a derivative of pyripyropene.

Culturing a Pyripyropene Producer Organism:
Biomass comprising at least one pyripyropene can be produced by fermentation of pyripyropene producer organisms. Pyripyropene producer organisms are any kind of microbial cells having the capacity to produce pyripyropenes, either by their natural set of genes or because they are recombinant for genes which provide for one, several, or all steps of the biosynthesis of at least one pyripyropene.

Examples of suitable pyripyropene producer organisms as well as their respective culture conditions have been described, in Pure Appl. Chem., vol. 71, No. 6, pp. 1059-1064, 1999; in Bioorganic Medicinal Chemistry Letter vol. 5, No. 22, p. 2683, and in Japanese Patent Application Laid Open No. 239385/1996, Japanese Patent Application Laid Open No. 184158/1994, WO 2004/060065, Japanese Patent Application Laid-Open No. 259569/1996.

Preferred pyripyropene producer organisms are microorganisms belonging to the genus *Penicillium*, the genus *Eupenicillium*, or the genus *Aspergillus*, Preferred species of pyripyropene producer organisms are: *Penicillium coprobium, Penicillium griseofulvum, Eupenicillium reticulospo-*

*rum* or *Aspergillus fumigatus* and in particular *Penicillium coprobium*. Preferred strains of these pyripyropene producer organisms are *Penicillium coprobium* PF-1169 strain (Journal of Technical Disclosure No. 500997/2008), *Penicillium griseofulvum* F1959 strain (WO2004/060065), *Eupenicillium reticulosporum* NRRL-3446 strain (WO2004/060065) and *Aspergillus fumigatus* FO1289, including its variant *Aspergillus fumigatus* FO1289-2501 (WO94/09147), among them *Penicillium coprobium* PF1169 being the most preferred.

Pyripyropene producer organisms usually produce more than one compound of Formula I, for example, WO94/109147 describes that *Aspergillus fumigatus* FO1289 is capable to procude Pyripyropene A, Pyripyropene B, Pyripyropene C and Pyripyropene D. Accordingly, it is possible to obtain one or several pyripyropenes from the dry biomass produced and used in the invention.

A pyripyropene producer organism can also be a microbial cell, for example *Aspergillus oryzae*, which comprises only parts of the genes for the biosynthetic pathway for production of pyripyropenes, but which is supplied with precursors of pyripyropene during fermentation conditions. Such microorganisms have, for example, been described in CA2787829 and CA2788058.

The pyripyropene producing organisms are preferably fermented in large quantities in liquid, such as in suspension cultures. Preferred methods are shake culturing under aerobic conditions, culturing with bubbling under stirring or deep part aerobic culturing, in particular, culturing with bubbling under stirring is in most cases of advantage.

The fermentation process is usually performed in bioreactors. Bioreactors typically allow for the control of culture conditions such as temperature, pH, oxygen tension, and carbon dioxide levels. For example, bioreactors are typically configurable, for example, using ports attached to tubing, to allow gaseous components like oxygen or nitrogen, to be bubbled through a liquid culture. The bioreactor may be pressurized. It may be also be adapted to allow the continuous or continual supply of the assimilable nitrogen and/or carbon sources. Bioreactors may comprise small volumes e.g. for lab scale applications, of 5 liter, 10 liter or 20 liter, but may also accommodate large volumes such as 5000 liter, 10.000 liter, 40.000 liter, 50.000 liter, 100.000 liter, 150.000 liter, 200.000 liter, or even higher volumes. The fermentation can be a continuous process, with regular harvesting or removal of the produced biomass or can be a batch process, such as a repeat fed batch process including one or more additions of carbon and/or nitrogen sources after fermentation has begun. Thus the fermentation process can be stopped or halted, and the produced biomass removed from the culture vessel, before another process or fresh fermentation is started. The carbon and nitrogen sources may be provided in separate compositions. This is because the different sources may be subject to different sterilizing conditions, and furthermore it allows a variation in the relative amounts of carbon and nitrogen or other nutrients during fermentation. The different nutrient sources can be supplied separately, or supplied simultaneously, or supplied as a combined preparation and are preferably provided in a liquid.

The nutrient sources may be complex sources, defined media or individual or isolated compounds. Non-complex sources are preferred and so the compounds may be added in a high degree of purity, and can be common (or commercially available) chemicals.

Suitable nitrogen sources include ammonia or ammonium ions. The advantage here is that ammonia can act as a pH regulant. This may be supplied in the form of an ammonium salt, such as nitrate, sulphate or phosphate or in the form of ammonium ions themselves, for example an aqueous solution of ammonium hydroxide. Other inorganic nitrogen sources can also be used, such as sodium nitrate, urea or an amino acid such as asparagine or glutamine. If the fungus is of the genus *Rhizopus* then nitrate is preferably not used as a nitrogen source. Complex nitrogen sources include yeast hydrolysates, primary yeast, soy bean meal, hydrolysates of casein, yeast, yeast extract or rice bran.

The carbon source can comprise complex sources such as maltodextrin, oat flour, oat meal, molasses, vegetable (e.g. soy bean) oil, malt extract or starch. Preferred carbon sources are noncomplex carbon sources such as, sugars, such as fructose, maltose, sucrose, xylose, mannitol, glucose, lactose, citrate, acetate, glycerol or ethanol.

The aqueous liquid may additionally contain other substances to assist in the fermentation, for example a chelating agent (e.g. citric acid), an anti-foaming agent (e.g. soy bean oil), a vitamin (e.g. thiamine and/or riboflavin), any necessary catalytic metals (for example, alkali earth metals such as magnesium or calcium, or zinc or iron and/or other metals such as cobalt and copper), phosphorus (e.g. phosphate) and/or sulphur (e.g. sulphate). Preferably the aqueous liquid will have a low sulphur content, for example less than 3.0 g/l, preferably less than 2.0 g/l, or 1.0 g/l of sulphur.

Preferably, the pH, temperature and/or oxygen content (of the aqueous liquid) during fermentation is controlled. This may be to keep the pH, temperature and/or oxygen content constant or within a desired range. The pH of the aqueous liquid during fermentation may be from pH 2 to pH 8, such as from pH 3 to pH 7, optimally from pH 4 to pH 6, but can also be for example from pH 6 to pH 8.

The temperature of the aqueous liquid during fermentation may be from 15° C. to 40° C., or from 18° C. to 40° C., such as from 20° C. to 35° C., optimally from 25° C. to 33° C. In many cases, the growth takes place around 26° C. to 37° C.

It is important that during fermentation mixing occurs. This may be achieved by aeration e.g. by bubbling air into the aqueous liquid. This may serve the additional purpose of providing oxygen to the growing cells. Other means of agitation or mixing include stirring, for example using an impeller. The energy input via stirring should usually be adjusted to a value between 1 to 20 W/L and preferably to a value of 2 to 5 W/L.

The stirring may result in a hydrofoil axial flow or may be designed in a way that the aqueous medium is forced radially outwards from the impeller, e.g. similar to a flow in a turbine. One of the advantages of aeration and/or agitation is that the oxygen content of the aqueous liquid can be kept relatively high. This may be at least 10%, such as at least 15%, optimally at least 20% (in terms of air saturation).

The production of pyripyropenes varies depending on the medium and culturing conditions, or the used organism. Accordingly, the fermentation may take from 1 to 40 days, such as from 5 to 20, or 10 to 18 days, but may optionally also be shorter e.g. from 2 to 4 days. Usually the fermentations conditions are selected in order be similar or identical to the fermentation conditions preferred by the cultured organism during production of pyripyropene. The accumulation of pyripyropenes usually reaches its peak in 2 days to 25 days. A shorter fermentation lends itself towards a batch, rather than a continuous fermentation process.

In a preferred embodiment, the utilizable sugar content is adjusted to a maximum of 5 g/l, preferably to a maximum of 1 g/l towards the end of fermentation, i.e. no sugar is added and fermentation is stopped only when the sugar content is equal to or below this value.

In one embodiment of the invention, the biomass produced during the fermentation is directly transformed into dry biomass via spray drying of the culture broth comprising the biomass. Preferably, the cells of the biomass are killed, e.g. by a method described below, before the drying step is performed.

In other embodiments of the invention, the biomass produced during the fermentation is separated from the culture broth, in order to produce wet biomass which is then used to produce dry biomass.

Killing the Cells

The biomass produced during fermentation is preferably killed before its separation from the culture broth, but can also be killed at a later stage of the processes of the invention. The cells of the biomass can be killed by processes known in the art. Preferably, the cells are killed via a thermal treatment directly after fermentation. Thermal treatment can be carried out in the culture vessel or in a dedicated apparatus. In some embodiments of the invention, killing may also be carried out in a continuously ran apparatus with a certain residence time. If thermal treatment is used, then freezing is one possibility although heating is generally preferred (e.g. pasteurization). Killing the cells via heating is usually performed at a temperature between 60° C. to 120° C., preferably between 70° C. to 90° C. for a timespan between 5 to 180 minutes, preferably for a timespan between 30 to 90 minutes.

Heat input into fermentation broth can be achieved by heat exchanger apparatus like plate heat exchangers or pipe heat exchangers or heating coils but also by mixing of substances such as water at elevated temperatures. One example for such mixing of substances is injection of water steam.

Temperatures for killing pyripyropene containing biomass may vary from 40° C. to 200° C. but preferably from 50 to 120° C. and even more preferably from 60 to 80° C. Corresponding residence time at elevated temperature in the apparatus for killing biomass will have to be adapted by routine experimentation to the conditions of each individual case, e.g. volume and design of the culture vessel or the apparatus dedicated to the killing of cells as well as the organism providing the biomass. Typically, the residence time is selected from 1 to 500 minutes or from 10 to 120 minutes or from 5 to 80 minutes. Alternatively, the cells of the biomass can be killed by chemical treatments. Such chemical treatments are readily available in the art. For example, benzoic acid or sodium acid, usually kill the cells if added to the fermentation broth in amounts from 0.1% to 10% (volume/volume).

Alternatively, or in addition thereto, the microorganisms can be killed after the separation of the biomass from the culture broth, or while being re-suspended in an organic resuspension medium, or after separation of the biomass from an organic resuspension medium, or during homogenisation of the biomass, or during drying of the biomass, or by a combination of these possibilities.

Separation of Biomass:

The biomass produced during the fermentation process can be separated from the culture broth by processes known in the art. The biomass may be separated from the total volume of the culture broth, or may be separated from only parts of the total volume, to allow for continuous fermentation. The separation of the biomass can be effected by established methods, preferably by filtration or centrifugation, e.g. by ultrafiltration, microfiltration, decanting, or a combination of filtration and centrifugation.

Filtration can be performed by employing the usual filters technologies used in the art, such as a vibratory separator, a vibrating screen filter, a circular vibratory separator, a rotary drum filter, a linear/inclined motion shaker, a pressure strainer, by tangential flow filtration, via belt filters, rotary filters, filter presses, or similar techniques in which a barrier consisting of the filter separates the biomass and allows the liquid phase without biomass to pass. Depending on the filter technique used, the filtration process is usually performed at a pressure of about 0.5 to 15 bar e.g. in case a filter press is used, or is performed at a pressure below normal, like 0.01 to 0.9 bar, e.g. in case a rotary drum filter is used.

The temperature used during separation oft the biomass is usually between 5° C. to 80° C., but can also be higher, in particular if the cells of the biomass are killed via the application of heat and the biomass is separated from the culture broth before the biomass and the culture broth had been time to cool down.

The vibratory separator can include at least one vibrating screen filter. The biomass should also not adhere significantly to the filter material. Preferred filter material is: porous ceramics or polypropylene the use of other material is possible as well.

One example of filtration that is in particular suitable for the present invention is tangential flow filtration, also known as cross-flow filtration. Tangential Flow Filtration (TFF) is a separation technique which uses membrane systems and flow force to purify solids from liquids. Preferred pore sizes used in TFF allow solutes and debris in the fermentation broth to flow through, but retain the biomass.

Suitable mesh sizes for the filtering procedure include smaller than 1000 micrometers, or smaller than 800 micrometers, or smaller than 600 micrometers, or smaller than 500 micrometers, or smaller than 400 micrometers, or smaller than 300 micrometers, or smaller than 200 micrometers, or smaller than 180 micrometers, or smaller than 150 micrometers, or smaller than 120 micrometers, or smaller than 100 micrometers, or smaller than 90 micrometers, or smaller than 80 micrometers, or smaller than 70 micrometers, or smaller than 60 micrometers, or smaller than 50 micrometers, or smaller than 40 micrometers, or smaller than 30 micrometers, or smaller than 20 micrometers. In some embodiments, a 106-micrometer vibrating screen filter is used. A filter with a mesh size other than 106 micrometers, or filters of other than a vibrating-type can also be used.

In certain embodiments, the filtering is performed at room temperature and at atmospheric pressure. In other embodiments, the filtering is performed at elevated or lowered temperatures and/or pressures.

Centrifugation is a process that involves the use of centrifugal force for the separation of mixtures. The more dense components of the mixture migrate away from the axis of the centrifuge, while the less dense components of the mixture migrate towards the axis. By increasing the effective gravitational force (i.e., by increasing the centrifugation speed), more dense material, usually solids, separate from the less dense material, usually liquids, according to density. Preferred machines for centrifugation are decanter centrifuges and high-speed disc stack centrifuges.

A decanter centrifuge can operate by pumping the culture broth including the biomass into a spinning cylinder. As the centrifugal force pushes the biomass against the outer wall, an internal rotating scroll can move the biomass against the wall towards the discharge at one end. The discharge end of the decanter centrifuge can have a diminishing radius along with the scroll to match the diminishing size. As the biomass moves up the ramp created by the diminishing radius, the biomass can be continuously removed.

A high-speed disc stack centrifuge can push the culture broth outwards along a path of slanted discs. The biomass comprised by the culture broth will be pushed on the downward slope of the discs and be separated from the culture broth. The biomass can be discharged either continuously or intermittently on the downwards side of the high-speed disc stack centrifuge, while the culture broth is pushed upwards along the discs to the outlet.

The biomass having been separated from the culture broth (wet biomass) usually contains more than 95% (weight/weight) of the pyripyropenes produced in fermentation, preferably more than 97% and more preferably more than 99%. The content of pyripyropenes in the separated culture broth is therefore usually less than 5% (weight/weight), preferably less than 3% and more preferably less than 1%.

The dry biomass used for isolation of pyripyropenes can be directly produced by drying the wet biomass gained via the techniques described above. These techniques usually produce a wet biomass having a content of residual water (weight/weight) between more than 15% to less than 90%. Preferably between more than 30% to less than 90%, even more preferred between more than 40% to less than 90% or between more than 50% to less than 90%.

However, it is not necessary, but usually of advantage to reduce the water content of the wet biomass even further before the wet biomass is used to produce dry biomass.

Hence, the wet biomass may be subjected, to a (further) liquid removal step involving the use of mechanical pressure directly applied to the wet biomass. The amount of mechanical pressure applied should not cause a significant percentage of the microbial cells of the biomass to rupture, if that would result in loss of pyripyropenes to the liquid phase, but should instead simply be enough to dewater the biomass to the level desired for subsequent drying. Accordingly, the wet biomass does usually still contain more than 95% (weight/weight) of the pyripyropenes produced in fermentation, preferably more than 97% and more preferably more than 99%. The content of pyripyropenes in separated liquid phase is therefore usually less than 5% (weight/weight), preferably less than 3% and more preferably less than 1% of the pyripyropenes produced during fermentation.

Mechanical pressure can be employed to the wet biomass, by using methods known in the art, for example by using a belt filter press, a screw press, a finisher press, a filterpress, a pressure strainer or any other means suited for the purpose. Preferably a belt filter press is used for the purpose.

A belt filter press is a dewatering device that applies mechanical pressure to a slurry or paste (e.g. the wet biomass) that is passed between two tensioned belts usually having small micron size openings. The tensioned belts run through a serpentine of decreasing diameter rolls. Most belt filter presses have three different zones: a gravity zone, where free liquid is drained by gravity through a porous belt; a wedge zone, where the solids are prepared for pressure application; and a pressure zone, where adjustable pressure is applied to the gravity drained solids. The belts can then pass through a series of rollers that squeeze the juice out through the openings in the belt. The caked solids can then be ejected where the two belts separate at the end of the unit operation. The juice can drip into pans at the bottom of the unit where using gravitational force it can be ejected through a common opening and sent downstream for further processing.

A screw press can operate by introducing material (e.g. the wet biomass) into a device that resembles a screw auger. The rotating shaft on the screw press can convey the material into the equipment, where as the material progresses, the flighting, or distance between the threads of the screw, gets smaller or the shaft getting wider. As the flighting decreases in distance, the total volume in between the threads decreases, creating a compression effect. The wet biomass can be compressed between these flights and liquid can be expelled. The rotating shaft can be encased by a mesh screen of small micron size that can hold the wet biomass in the screw but allow the liquid to be expelled.

A finisher press can operate similar to the screw press, but instead of a screw with threads, there is a rotating shaft with paddles that can push the material along a screen size. The remaining solid phase of the wet biomass can then be ejected out of the finisher press. A filter press, including filter presses designed as a chamber filter press or a membrane filter press, can operate by using a positive displacement pump and pumping the wet biomass into a series of filter chambers. The filter chambers can have small micron size openings that can push liquid out using the pressure of the positive displacement pump. Once enough solids have accumulated inside the filter and liquid cannot be extracted further, a "squeeze" can be introduced by injecting water or air into bladders in between the filter chambers, creating additional pressure on the filter cake when using a membrane filter press. As the bladders push outwards, additional pressure can be exerted on the filter chambers as the walls push inwards. Additional liquid can be liberated. Once the liquid is sufficiently removed, the filterpress chambers can be opened and the wet biomass can be ejected One or more of the above techniques to apply mechanical pressure can be used alone or in combination to remove liquid from the wet biomass for use in the present invention.

Hence, the processes to obtain at least one pyripyropene and the processes to produce a derivative of pyripyropene, can comprise a step of separation of biomass from the culture broth to obtain wet biomass, which is then used to produce dry biomass.

The step to obtain wet biomass can be performed via filtration, via centrifugation preferably using a technology as described above, or can be performed via a combination of filtration, and centrifugation and may or may not comprise a step of application of mechanical pressure, again preferably a step of application of mechanical pressure as described above. Accordingly, the processes to obtain at least one pyripyropene and the processes to produce a derivative of pyripyropene, can comprise a step of separation of biomass from the culture broth by using a vibratory separator, a vibrating screen filter, a circular vibratory separator, a rotary drum filter, a linear/inclined motion shaker, a pressure strainer, tangential flow filtration, via belt filters, rotary filters, filter presses, of which a vibratory separator and tangential flow filtration are preferred. Preferred machines for centrifugation are decanter centrifuges and high-speed disc stack centrifuges In some embodiments, the wet biomass produced as described above is further treated to reduce the water content by using a step of application of mechanical pressure, by using a belt filter press, a screw press, a finisher press, a filterpress, or a pressure strainer. Preferably a belt filter press is used for the purpose.

Reduction of Unwanted Components and/or Short Term Storage:

In most embodiments of the invention, the wet biomass produced via separation from culture broth or after application of mechanical pressure is directly used to produce dry biomass, which is then used either for storage or for purification of pyripyropenes.

However, in various embodiments of the invention, the wet biomass is further purified during the handling of the wet biomass in order to reduce contents of the culture broth which could cause problems of purification of pyripyropenes or the handling of the wet biomass in later stages and/or is subjected to short term storage in a storage tank.

Contents of the culture broth which could be reduced by further purification of the wet biomass are for example, salts, residual sugar, or other components which have been produced during fermentation, e.g. lipophilic components, like fatty acids and oils.

Accordingly, the further processing of the wet biomass may or may not involve one or more washing steps for further purification, in which the wet biomass is re-suspended in a medium in which the solubility of pyripyropenes is very low (resuspension medium). Accordingly, the medium used for a washing step is preferably hydrophilic, or may consist of a mixture of hydrophilic of hydrophobic components. In one embodiment the resuspension medium is water. In another embodiment the resuspension medium is an aqueous solution of a pH-buffer, for example phosphate salt or TRIS or ammonia salt, or an aqueous solution of a preservating agent like benzoic acid, benzoic acid salts, sobic acid, sorbic acid salts or other preservatives known in the art to have the same effect.

Preferably, the wet biomass is re-suspended directly after separation from the culture broth and not after the application of mechanical pressure.

The temperature of the re-suspension medium can vary between the freezing and the boiling point of the resuspension medium, preferably the temperature is between 5° C. and 50° C., more preferred the temperature is between 10° C. and 30° C. The resuspension medium can be separated from the biomass by using identical or similar technologies as can be used to separate the biomass from the culture broth. The biomass can be resuspended several times in the same or in different resuspension media. Usually the volume of a resuspension medium is less than 70%, 60%, 50%, 30%, 25%, 10% or less than 5% of the volume of the culture broth used to produce the respective amount of wet biomass, but may even be larger, like 1 times, 2 times, 3 times or more of the volume of the wet biomass. The wet biomass produced after separation from the culture broth, after one or more resuspension steps or produced after application of mechanical pressure can be stored at a storage tank, preferably a chilled storage tank. In particular embodiments the chilled storage tank is maintained at a temperature below 50° C., or below 40° C., or below 30° C., or below 25° C., or below 20° C., or below 15° C., or below 10° C., or below 5° C., or below 2° C., but above freezing temperature of the wet biomass. The chilled storage tank is maintained at a temperature below room temperature, preferably below 15° C., or below 10° C., or below 5° C., or below 2° C., but above freezing temperature of the wet biomass.

The wet biomass may be stored under such conditions for several hours and up to several month, e.g. during shipping. Preferred durations for short term storage are more than 5 hours to 5 month, but should preferably not exceed one or two month, in case the wet biomass comprises living cells of the wet biomass itself or of other microorganisms introduced during handling of the wet biomass. A further way to stabilize the wet biomass for storage is to lower the pH of the wet biomass for, or during storage to a pH from 1 to 5. Biomass stabilized in this way can usually be stored for a term between several days to several weeks. It is also possible to combine both methods, i.e. storage at a lowered pH and in a chilled storage tank, in order to prolong the storage time.

Homogenisation:

The wet biomass is directly used for further drying, or can be homogenized before a further step is taken to either dry the wet biomass or to enhance the content of dry matter of the biomass, e.g. by applying mechanical pressure. In particular in case the wet biomass has a comparatively low content of dry material (weight/volume) of less than 30%, 25%, 20%, 15%, 10%, or 5% and/or had been stored for some time, it is advisable to homogenize the biomass before drying, or before further mechanical pressure is applied. The homogenization can simply have the aim to produce a homogenous distribution of solid and liquid components of the wet biomass in order to facilitate further processing, e.g. to provide a homogenous supply of wet biomass to a belt filter press, a screw press, a finisher press, a filterpress, or any other means suited to enhance the content of dry matter, or can have the aim to provide a homogenous supply of wet biomass for further drying, e.g. as feed to a paste mill dryer, a spray dryer, a flash dryer, a fluid bed dryer, or a rotary dryer.

A homogenous distribution of solid and liquid components as well as a disruption of cell walls of the wet biomass can be achieved by using a rotor stator dispersing machine or other homogenisation apparatus. A rotor stator dispersing machine is a preferred means to homogenize wet biomass having a comparatively low content of dry matter, such as a content of dry material of less than 30%, 25%, 20%, 15%, 10%, or 5%.

An expander or extruder can be used to shape and/or homogenize the wet biomass. An extruder is preferred because extrusion conditions can be adjusted to minimise disruption of cell walls. Extrusion may be used to form elongate cylinder like structures (these may have a cylindrical and/or of circular cross-section) if passed through a suitable die-plate (e.g. with circular or square holes). These elongate structures can further be formed into granules, by using a cutter, such as a rotating blade, to cut the long strands of cylinder like structures. Following extrusion the "spaghetti" and granules preferably have a water content of less than 15%, such as less than 10%, and optimally from 3 to 7%. The granules may have a diameter of from 0.3 to 10 mm, such as from 0.7 to 5 mm, optimally from 1 to 3 mm. Extrusion can also be used to form sheets or layers of the wet biomass. This can be achieved by passage through one or more slots. These forms may also be prepared by the use of one or more moving surfaces, such as roller(s) and/or cylinder(s). These may be moving in the same direction or counter-rotating and there may be one, two or up to five such surfaces. The sheets or layers may have a thickness of from 0.3 to 10 mm, such as from 0.7 to 5 mm, optimally from 1 to 3 mm.

Wet biomass treated by extrusion is preferably dried in a fluidized bed drier to produce dry biomass.

In some embodiments of the invention it may be of advantage to use the homogenization step to disrupt the cell walls of the wet biomass. As used herein, disruption of cell walls encompasses mechanical or chemical procedures that disturb the organization of the organism on the level of individual cells or multicellular structures. Disruption of cell walls can include, for example, milling, chopping, shredding, smashing, pressing, tearing, lysis by osmotic pressure, or chemical treatments that degrade biological structures. Merely by way of example, disruption of the cell walls can be achieved using a milling stage, e.g. by applying a knife mill, a ball mill, and the like, or a combination thereof.

The processes to obtain at least one pyripyropene and the processes to produce a derivative of pyripyropene, can comprise a further step in which the wet biomass is treated to reduce unwanted components, for example by resuspension in a resuspension medium, and or a step of short term storage and/or a step of homogenization, before the wet biomass is used to produce dry biomass.

Accordingly, the processes as described above, may comprise a step in which the wet biomass has been re-suspended in a resuspension medium and/or has been homogenized and/or has a glucose content of less than 5 g/l, and/or has a water content between more than 15% to less than 90%.

Production of Dry Biomass:

The dry biomass used to isolate pyripyropenes has, in the order of preference, content of residual water of less than 15%. More preferred, the dry biomass has, in the order of preference, a content of residual water of less than 10%, 9%, 8%, 7%, 6%, 5%, 4% or 3%. The content of residual water is measured according to the method of, again in the order of preference the Aufhäuser method, the halogen (IR) scales method and/or the Karl-Fischer method, as described in the Examples.

The production of dry biomass can be performed by using a spray dryer, a paste mill dryer, a flash dryer, a fluid bed dryer, or a rotary dryer, or by any other means suitable to dry the wet biomass to the residual water content described above, such as lyophilization or by the use of simple tray dryers. Preferred methods to produce dry biomass are by drying in a spray dryer or a paste mill dryer.

Dry biomass can be produced from wet biomass produced by any kind of process for separation of biomass from the culture broth described above, including further steps to reduce the water content of the wet biomass, like the application of mechanical pressure. However, dry biomass can also be produced by drying biomass which has not been separated from the culture broth used in fermentation e.g. by using a spray dryer.

Spray drying is a commonly used method of drying a liquid feed using a hot gas. A spray dryer takes a liquid stream, e.g. the wet biomass and separates the solute as a solid and the liquid into a vapor. The input stream is sprayed through a nozzle into a hot vapor stream and vaporized. The nozzle of the spray dryer is usually adjustable, and typically is adjusted to make the droplets as small as possible to maximize heat transfer and the rate of water vaporization. However, the nozzle has to be adjusted in order to avoid blockage by parts of the biomass comprised by the input stream. Preferably the biomass of the input stream is homogenized in order to produce smaller particles and to disrupt the cell walls before it is used as input stream for spray drying. The resulting dry solids may have a fine, powdery consistency, depending on the size of the nozzle used.

It is not possible to provide herein precise values for each parameter involved in adjusting the conditions for spray drying, since these parameters and their associated values depend on the type of spray-drying device used. As a guide, the spray drying process is best used with wet biomass having a residual water content of 80% to 99.5%, preferably 88% to 92% (weight/weight), but can also be used to produce dry biomass directly from biomass still comprised in the culture broth of fermentation.

The nozzle should have an opening of 0.5 to 10 mm. The pressure applied at the end of the nozzles for spraying the wet biomass may be between about 2 to 250 bar, and the hot air pressure at the inlet of the device may be between about 100 and 2000 mbar over pressure.

The inlet air temperature is preferably between 80° C. to 350° C., preferably 120° C. to 180° C. The outlet temperature is preferably between 20° C. to 200° C., preferably between 60° C. to 100° C.

Flash dryers are typically used for drying solids that have been de-watered or inherently have low moisture contents. Flash dryers, also known as "pneumatic dryers", are usually used to dry wet biomass having a residual water content of 20% to 90% (weight/weight) These dryers typically disperse wet material into a stream of heated air which conveys it through a drying duct. The heat from the airstream dries the material as it is conveyed through the drying duct. More detailed descriptions of flash dryers and pneumatic dryers can be found in U.S. Pat. No. 4,214,375, which describes a flash dryer, and U.S. Pat. Nos. 3,789,513 and 4,101,264, which describe pneumatic dryers.

A flash dryer can drop the wet biomass into a closed loop system with hot air injected tangentially to the outside of the loop. The heated air can convey the wet biomass along the outer edge of the loop, thereby drying continuously.

By having the material roll along the wall driven by the air flow, a particle-size reducing effect can be created once the size of the particles is small enough they can flow freely off the air. Once the particle size and water content are reduced to the desirable levels, the particles can be carried along an exhaust pipe located at the inside portion of the loop to a collection apparatus.

Paste mill dryers are used for drying of wet cake, slurry, or paste which is normally difficult to dry in other dryers. Preferably they are used to dry wet biomass having a residual water content of 5% to 80% (weight/weight).

A paste mill dryer can dry wet biomass into an agitated vat that causes the material to be suspended due to the air pressure which creates a suspension effect. The material is fed by a screw feeder through a variable speed drive into the vertical drying chamber where it is heated by air and at the same time disintegrated by a specially designed disintegrator, which is usually a fan-like structure that rotates in the drying chamber, thereby fulfilling a function like a spinning mixer. The heating of air may be direct or indirect depending upon the application. The dry biomass which occurs in size-reduced particles can then be carried through a classifier at the top of the drying chamber carried by air flow into a collection apparatus such as a cyclone, bag-house, or the like, where the material is then collected.

Rotary dryers operate by continuously feeding wet material, e.g. the wet biomass, which is dried by contact with heated air, while being transported along the interior of a rotating cylinder, with the rotating shell acting as the conveying device and stirrer. Preferably they are used to dry wet biomass having a residual water content of 5 to 80% (weight/weight).

Fluid-bed dryers are usually used for simultaneous drying and disintegration of a material in the form of a paste. Fluid bed dryers can comprise a cylindrical drying chamber, which is provided with an upwardly conical bottom. The wet biomass is supplied to the chamber through a substantially circularly extending slit between the conical bottom and the wall of the drying chamber from an annular distributor for the fluidization and drying medium. A stirrer is placed coaxially in the chamber, the blades of said stirrer being parallel to the conical bottom. Preferably, the blades of the stirrer are positioned at a small distance from the conical bottom. An example for a fluid bed dryer is disclosed in U.S. Pat. No. 4,581,830. A different design of a fluid bed dryer can operate and dry material (e.g., wet biomass) by introducing it onto a vibrating bed with heated air passing directly or indirectly to the material. The vibration and air can create a fluidized suspension of the material that can increase the surface area to be dried. Preferably they are used to dry wet biomass having a residual water content of 5% to 80% (weight/weight).

The drying procedure, in particular drying procedures using a flash dryer, a paste mill dryer, a rotary dryer, a fluid-bed dryer or a tray dryer or the like, or a combination thereof, use an air stream for drying having an inlet temperature (the temperature at the entrance to the dryer) of above 25° C., or above 50° C., or above 75° C., or above 100° C., or above 125° C., or above 150° C., or above 175° C., or above 200° C., or above 225° C., or above 250° C., or above 275° C., or above 300° C., or above 325° C., or above 350° C., or above 375° C., or above 400° C., or above 425° C., or above 450° C., or above 475° C., or above 500° C.

Preferably, the inlet temperature is from 25° C. to 50° C., or from 50° C. to 75° C., or from 75° C. to 100° C., or from 100° C. to 125° C., or from 125° C. to 150° C., or from 150° C. to 175° C., or from 175° C. to 200° C., or from 200° C. to 225° C., or from 225° C. to 250° C., or from 250° C. to 275° C., or from 275° C. to 300° C., or from 300° C. to 325° C., or from 325° C. to 350° C., or from 350° C. to 375° C., or from 375° C. to 400° C., or from 400° C. to 425° C., or from 425° C. to 450° C., or from 450° C. to 475° C., or from 475° C. to 500° C., or above 500° C.

In some embodiments, the inlet temperature is from 50° C. to 100° C., or from 100° C. to 150° C., or from 150° C. to 200° C., or from 200° C. to 250° C., or from 250° C. to 300° C., or from 300° C. to 350° C., or from 350° C. to 400° C., or from 400° C. to 450° C., or from 450° C. to 500° C., or above 500° C.

In some embodiments, the outlet temperature (the temperature at the exit from the dryer) is below 300° C., or below 275° C., or below 250° C., or below 225° C., or below 200° C., or below 175° C., or below 150° C., or below 125° C., or below 100° C., or below 75° C., or below 50° C., or below 25° C.

In some embodiments, the outlet temperature is from 300° C. to 275° C., or from 275° C. to 250° C., or from 250° C. to 225° C., or from 225° C. to 200° C., or from 200° C. to 175° C., or from 175° C. to 150° C., or from 150° C. to 125° C., or from 125° C. to 100° C., from 100° C. to 75° C., or from 75° C. to 50° C., or from 50° C. to 25° C., or below 25° C.

In some embodiments, the outlet temperature is from 300° C. to 250° C. or from 250° C. to 200° C., or from 200° C. to 150° C., or from 150° C. to 100° C., from 100° C. to 50° C., or from 50° C. to 25° C., or below 25° C.

In some embodiments, the air used for drying is replaced by non-flammable gas, for example nitrogen ($N_2$). This is of particular importance, if the dry biomass produced via the drying process has a high proportion of small particle sizes.

Tray dryers are typically used for laboratory work and small pilot scale drying operations. Tray dryers work on the basis of convection heating and evaporation. Wet biomass can be dried effectively using heat and an air vent to remove evaporated water. Hot air is circulated to dry. Tray dryers can also employ reduced pressure or vacuum to dry at room temperature when products are temperature sensitive and are similar to a freeze-drier but less costly to use and can be easily scaled-up.

Alternatively to the drying techniques described above, the dry biomass can also be produced by lyophilization, also known as freeze drying or cryodessication. The lyophilization process involves the freezing of the material and then reducing the surrounding pressure and adding enough heat to allow the frozen water in the material to sublime from the solid phase to gas. Similar to the use of tray dryers, lyophilization is mostly used for small pilot scale operations, which are less preferred embodiments of the invention.

Various flow agents (including silica-derived products such as precipitated silica, fumed silica, calcium silicate, and sodium aluminum silicates) can be added to the biomass before or after drying. Application of these materials to high fat, hygroscopic or sticky powders prevents caking or clumping during and after drying, and promotes free-flow of dry powders. This not only reduces sticking, but also reduces build up and oxidation of materials on dryer surfaces.

Dry Biomass:

As mentioned above, the dry biomass used to isolate pyripyropenes has, preferably, residual water content (weight/weight) of less than 10%, 9%, 8%, 7%, 6%, 5%, 4%, or 3%.

Preferably, the particle size of more than 80%, 85%, 90%, 95%, or more than 98% of the dry biomass is between 0.01 mm to 5 mm, or less than 3 mm, preferably less than 1 mm and more preferably less than 0.5 mm.

The average size of particles measured immediately after homogenation or as soon is practical thereafter is preferably no more than 10 µm, no more than 25 µm, or no more than 100 µm. In some embodiments, the average particle size is 1 µm to 10 µm, 1 µm to 15 µm, 10 µm to 100 µm or 1 µm to 40 µm. In some embodiments, the average particle size is greater than 10 µm and up to 100 µm. In some embodiments, the average particle size is between 10 µm to 100 µm.

Milling can be carried out on the dry biomass in order to produce a particular particle size, by means of mechanical systems with swiveling or fixed parts. Such parts may be hammers, screens, or rotating cylinders pressing on one another.

Exemplary techniques for separation of wet biomass from the culture broth, for applying mechanical pressure, for drying of the wet biomass or for milling are described for illustration purposes only, and are not intended to limit the scope of the application. A person of ordinary skill in the art, reading the description, would understand that other techniques can be employed to achieve the same results.

Storage of Dry Biomass:

The dry biomass produced via any of the techniques described above or produced by similar techniques can be stored in a storage tank. The storage tank is usually maintained at a temperature below 50° C., or below 40° C., or below 30° C., or below 25° C., or below 20° C., or below 15° C., or below 10° C., or below 5° C., or below 2° C., but preferably above freezing temperature.

The dry biomass may be stored under such conditions for several hours or may be stored for long term storage. The stored dry biomass has preferably a content of residual water (weight/weight) of less than 10%, 9%, 8%, 7%, 6%, 5%, 4%, or 3%.

Preferred durations for storage are from about 5 hours or up to several years. Even more preferred durations for storage are for more than about 5 hours to less than about one year, but it is also possible to chose other durations e.g. from about 1 week to about 12 month, from about 2 weeks to about 24 month, e.g. from about 1 month to about 18 month, from about 4 hours to about 6 month.

Hence, the processes to obtain at least one pyripyropene and the processes to produce a derivative of pyripyropene, uses dry biomass having a residual water content (weight/ weight) of less than 10%, 9%, 8%, 7%, 6%, 5%, 4%, or 3%, and might have been stored from about 5 hours or up to several years, before the comprised pyripyropene is obtained.

While every handling of the wet biomass before extraction of the produced pyripyropenes, including the steps to produce dry biomass, includes the risk of loosing valuable amounts of the biomass, it is possible to obtain a yield of at least 90%, 91%, 92%, 93%, 94%, 95%, 96%, 97%, 98% or even more of the pyripyropenes produced in fermentation via extraction, based on the amount of recovered dry biomass.

A further embodiment of the invention is dry biomass of a pyripyropene producer organisms comprising at least one pyripyropene and having a
a) water content of less than 10%, or
b) a particle size between 0.01 mm to 5 mm, or
c) has a water content of less than 10% and a particle size between 0.01 mm to 5 mm.

Preferably, the dry biomass having those features is from a pyripyropene producer organism belonging to the genus *Penicillium, Eupenicillium* or *Aspergillus*, even more preferred, being from *Penicillium coprobium, Penicillium griseofulvum, Eupenicillium reticulosporum* or *Aspergillus fumigatus*, in particular of one of their strains mentioned above. In one embodiment the dry biomass is from *Penicillium coprobium*, for example from *Penicillium coprobium* PF1169.

The dry biomass preferably comprises at least pyripyropene A, but may also comprise a combination of one or more pyripyropenes, for example the dry biomass may comprise Pyripyropene A, Pyripyropene B, Pyripyropene C and Pyripyropene D.

Extraction and Purification of Pyripyropenes:

The extraction of pyripyropenes from dry biomass can be performed according to methods known in the art e.g. as described in WO2004/060065, WO94/09147 or WO2011/108155.

Suitable solvents for extraction include:
alcohols having 1 to 6 carbon atoms such as methanol, ethanol, 1-propanol, 2-propanol, 1-butanol, 2-butanol, iso-butanol, tert-butanol, n-hexanol, and alcohols such as 2-ethyl-hexanol, hexafluoroisopropanol, ethylene glycol;
aromatic hydrocarbons such as benzene, toluene, ethylbenzene, chlorobenzene, cymene, xylenes, mesitylene, benzotrifluoride;
esters such as methyl acetate, ethyl acetate, n-butyl acetate, isobutyl acetate;
ethers such as diethyl ether, diisopropyl ether, di-n-butyl ether, tert-butyl methyl ether (TBME), tetrahydrofuran (THF), 2-methyl tetrahydrofurane, 1,4-dioxane, 1,2-dimethoxyethane;
dipolar aprotic solvents such as N,N-dimethylformamide (DMF), N,N-dibutylformamide, N,N-dimethylacetamide (DMAC), 1-methyl-2-pyrrolidinone (NMP), 1,3-dimethyl-2-imidazolidinone (DMI), N,N'-dimethylpropylene urea (DMPU), dimethyl sulfoxide (DMSO), sulfolane; acetonitrile;
polar organic solvents such as pyridine, halogenated hydrocarbon solvents such as dichloromethane and chloroform
ketones such as acetone, methyl ethyl ketone, diethyl ketone, cyclohexanone
nitriles such as acetonitrile and isobutyronitrile The term solvent as used herein includes also mixtures of two or more of the above solvents. The solvents are usually applied at a temperature in the range of from 0° C. to the boiling point of the solvent, preferably the solvents are applied at a temperature in the range of from 20° C. to 60° C.

In one embodiment of the invention the solvents used for extraction are organic solvent selected from the group consisting of methanol, methyl acetate, ethyl acetate, butyl acetate, toluene, ethylbenzene, chlorobenzene, chloroform, dichloromethane, diethyl ether, diisopropyl ether, tetrahydrofuran, and dioxane or a mixture of at least two of these solvents. In a further embodiment, the solvents include methanol, toluene and ethyl benzene or are a mixture of at least two of them, in particular methanol/toluene mixtures or methanol/ethylbenzene mixtures.

Usually the extraction is performed several times on the dry biomass, in order to extract the pyripyropenes as completely as possible. The solvent comprising extracted pyripyropenes is separated from the biomass via filtration.

The filter resistance depends on the particular solvent used and on the residual water content of the dry biomass used.

In some embodiments of the invention, the filter resistance is in rising degree of preference: below $5*10^{13}$ mPas/m$^2$, below $4*10^{13}$ mPas/m$^2$, below $3*10^{13}$ mPas/m$^2$, below $2*10^{13}$ mPas/m$^2$.

Methods to purify the pyripyropenes comprised in the solvent used for extraction are readily available in the art. Some exemplary methods have been described in WO94/09147, WO2004/060065 and WO2011/108155.

The pyripyropenes obtained via the processes described above can be used to create further derivatives of pyripyropenes, for example derivatives as described in EP1889540, EP2119361, EP2196815, EP2426124, in particular preferred are compounds of Formula III, Formula IV and Formula V.

A method for the production of the compound of Formula III is described in Japanese Patent Laid-Open Publication No. 259569/1996.

Methods for the production of compounds of Formula IV and Formula V are described in WO2006/129714.

Particular preferred methods for the production of a compound of Formula V is described in EP13151492.9 and U.S. 61/753,023 which are both included by reference in their entirety.

The invention also encompasses processes to obtain at least one compound of Formula I or to produce, at least one compound of Formula III, Formula IV or Formula V, from dry biomass having a
a) water content of less than 10%, or
b) a particle size between 0.01 mm to 5 mm, or
c) has a water content of less than 10% and a particle size between 0.01 mm to 5 mm.

Preferably, the dry biomass having those features is from a pyripyropene producer organism belonging to the genus *Penicillium, Eupenicillium* or *Aspergillus*, even more preferred, being from *Penicillium coprobium, Penicillium griseofulvum, Eupenicillium reticulosporum* or *Aspergillus fumigatus*, in particular of one of their strains mentioned above. In one embodiment the dry biomass is from *Penicillium coprobium*, for example from *Penicillium coprobium* PF1169.

The dry biomass preferably comprises at least pyripyropene A, but may also comprise a combination of one or more pyripyropenes, for example the dry biomass may comprise pyripyropene A, pyripyropene B, pyripyropene C and pyripyropene D.

Preferably, the processes involve obtaining a compound of Formula II, which may or may be not used to produce at least one compound of Formula III, Formula IV or Formula V, preferably used to produce at least one compound of Formula IV or Formula V and even more preferred a to produce a compound of Formula V. The processes may also comprise the step of using at least one compound of Formula II, Formula III, Formula IV or Formula V, preferably a compound of Formula V to produce a pest control composition, comprising at least one compound of Formula II, Formula III, Formula IV or Formula V. The pest control composition is preferably an insecticide.

Processes to obtain compounds of Formula III, Formula IV or Formula V from compounds of Formula I or Formula II, as well as processes to produce pest control compositions, including insecticides using these compounds as active ingredients are, for example, disclosed in EP2223599, EP2119361 and EP1889540, which are included herein in their entirety.

EXAMPLES

Example I: Production of Dry Biomass Having 7% Residual Water Content Via Drying in a Paste Mill Dryer and Extraction of Pyripyropene A with Ethyl Benzene For drying in a paste mill dryer and further extraction of pyripyropene A suspended biomass of *Penicillium coprobium* from fed batch fermentation was applied. The microorganism *P. coprobium* was cultivated in a 16.5 m³ fermenter with 10 m³ working volume.

The harvested culture broth comprised a volume of 10 m³ and contained 6 to 8% (weight/volume) of biomass which comprised 1.8% to 2% (weight/volume) of pyripyropenes, located inside the biomass. (For HPLC analytics of pyripyropene A and Biomass content determination see below)

The harvested culture broth was treated with a thermal inactivation procedure and dewatered by filtering in a filter press device containing 26 plates with a size of 760×760 mm to produce wet biomass. All plates were covered with filter cloth material of the manufacturer Nakao filter corp., type TR 2600. The obtained filter cake (wet biomass) had a water content of ~75% to 78% (for determination water content see below). Residual Glucose was not detected in the filter cake.

This dewatered filter cake was then subjected to drying in a paste mill dryer similar in construction to the schematic drawing of a paste mill dryer shown in FIG. 1.

The paste mill dryer used in Example I had the following specifications:

| | |
|---|---|
| Diameter: | 140 mm |
| Hight: | 1300 mm |
| No. of rotorknifes: | 5 |
| Max. turn number | 2800 RPM |
| Max. gas thoughput: | 300 kg/h |

7.5 to 7.9 kg/h of the described filter cake were fed into the paste mill dryer via a feed screw. The amount of the nitrogen used as drying gas was set to 119 to 121 m³/h or hydraulic gas velocity of 3 m/s, respectively. The rotor comprised in the drying chamber of the paste mill dryer was set to a turn number of 900 RPM to achieve a sufficient residence time in the apparatus corresponding to sufficient drying level of the product. The inlet temperature of the drying gas was set to 221 to 224° C.

The obtained water content of the dried biomass was determined to be 7% and the pyripyropene A content was 28.9 wt %.

The produced dry biomass showed long term storage stability at room temperature: after 213 days a loss of pyripyropene A of 4% was observed, and after 242 days in total 6% pyripyropene A had been decomposed. At 60° C. a continuous pyripyropene A degradation of in total 54% pyripyropene A was observed after 242 days.

Milling and Extraction with Ethyl Benzene:

The biomass obtained by paste mill drying as described above and containing 7% residual water was submitted to milling using a Microthron MB550 apparatus, set on step 7 for 45 seconds. 100 g of the milled dry biomass was submitted to a 0.75 L-reactor stirred with a blade impeller. 200 mL of ethyl benzene were added and the suspension was stirred for 18 h at 60° C. with 250 rpm. Afterwards the suspension was filtered using a 0.5 L glass filter (porous size 3, diameter 9.5 cm) using vacuum of 200 mbar. The filter cake was washed two times with 200 mL of ethyl benzene each having a temperature of 60° C. (displacement washings). Afterwards, the filter cake was washed two times with 150 mL of ethyl benzene each having a temperature of 60° C. (displacement washings). The pyripyropene was obtained at a yield of 93.9% (weight/weight) compared to the amount present in the dry biomass before extraction.

Example for the Procedure of the Filter Resistance Determination of Dried Biomass Using Different Extraction Solvents:

50 g of paste mill dried biomass having a residual water content of 7% (see Example I above) and 100 ml of solvent were stirred at a certain temperature for 18 hours. The solvents used were a) methanol having room temperature; b) toluene having room temperature, c) ethyl benzene having room temperature and d) ethyl benzene having 60° C. The obtained suspension was filtered using a pressure filter and a filter cloth PP25130F (PP=polypropylene, company: Verseidag) at 1 bar. The following parameters were measured to determine the filter resistance: a) filtration area, b) filtration time, c) filtration pressure, d) volume of obtained filtrate, e) height of the filter cake. Filter resistances and concentrations of pyripyropene A in solution after extraction determined for biomasses having different residual water contents are listed in Table 2).

TABLE 2

Summary of Pyripyropene (PPA) extractions from wet and dry biomass

| Entry | Method | Residual $H_2O$ [%] | Solvent itself or for extraction | T [° C.] | Filter resistance [mPas/m²] | Concentration of PPA after extraction[6] [wt %] |
|---|---|---|---|---|---|---|
| 1 | Direct extraction of fermentation broth | 90-95[1] | Water[5] | RT | $2.6 * 10^{14}$ | ~1 |

TABLE 2-continued

Summary of Pyripyropene (PPA) extractions from wet and dry biomass

| Entry | Method | Residual $H_2O$ [%] | Solvent itself or for extraction | T [° C.] | Filter resistance [mPas/m$^2$] | Concentration of PPA after extraction[6] [wt %] |
|---|---|---|---|---|---|---|
| | | | Toluene | RT | $4.8 * 10^{14}$ | |
| | | | Ethylbenzene | RT | not determined | |
| 2 | Extraction of filter cake | ~75[2] | MeOH | RT | $6.3 * 10^{13}$ | ~1 |
| | | | MeOH | RT | — | |
| | | | Ethylbenzene | 60 | $6.2 * 10^{13}$ | |
| 3 | Paste mill drying | 7[3] | MeOH | RT | $0.8 * 10^{13}$ | >4 |
| | | | Toluene | RT | $2.0 * 10^{13}$ | |
| | | | Ethylbenzene | RT | $3.2 * 10^{13}$ | |
| | | | Ethylbenzene | 60 | $1.0 * 10^{13}$ | |
| | | 5[3] | MeOH | RT | $1.6 * 10^{13}$ | |
| | | | Toluene | RT | $4.6 * 10^{13}$ | |
| | | | Ethylbenzene | RT | $4.4 * 10^{13}$ | |
| | | | Ethylbenzene | 60 | $1.4 * 10^{13}$ | |
| 4 | Spray drying | 3[4] | MeOH | RT | $0.9 * 10^{13}$ | |
| | | | Toluene | RT | $2.5 * 10^{13}$ | |
| | | | Ethylbenzene | RT | $2.8 * 10^{13}$ | |
| | | | Ethylbenzene | 60 | $1.0 * 10^{13}$ | |

[1]filtration of ~15 g ferm. broth 2x washing of the filter-cake w/ distilled water; drying of the filter cake: IR-scales (Mettler Toledo) at 180° C. until constant weight
[2]by calculation from biomass content of fermentation broth and the actual weight of the filter cake
[3]IR scales, 102° C., 4 h
[4]Karl Fischer
[5]Water in this case means that the fermentation broth itself was taken for filtration and not further diluted by any extraction solvent or water.
[6]yield ~>90%; washings included Example II: Production of Dry Biomass Having 5% Residual Water Content Via Drying in a Paste Mill Dryer and Extraction of Pyripyropene A with Toluene and Ethyl Benzene The same material and apparatus as described in Example 1 was used for drying in a paste mill dryer. The Feed rate was set this time to 4 to 5.8 kg/h and the rotor speed was set to 1000 RPM. 113 to 117 m$^3$/h of drying gas (nitrogen) were applied at 219 to 224° C. to dry the wet biomass.

The dry biomass generated in the described drying process had a residual water content of 5%, a pyripyropene A content of 28% and showed long term storage stability at room temperature. A loss of pyripyropene A of 4% was observed after 183 days, after 242 days a total of 11% pyripyropene A had been decomposed. Storage of the same Material at 60° C. for the same amount of time (242 days) produced a loss of 11% pyripyropene A.

Milling and Extraction with Toluene:

Dry biomass obtained by paste mill drying, as described above, containing 5% residual water was submitted to milling using a Microthron MB550 apparatus, set to step 7 for 45 sec. 100 g of the milled dry biomass was submitted to a 0.75 liter-reactor stirred with a blade impeller. 200 ml of toluene were added and the suspension was stirred for 18 h at 60° C. with 250 rpm. Afterwards the suspension was filtered using a 0.5 liter glass filter (porous size 3, diameter 9.5 cm) using vacuum at 200 mbar.

The filter cake was washed with 200 ml of toluene (displacement washing). Afterwards, the filter cake was transferred to the 0.75 liter reactor and stirred for further 60 min with 200 ml of toluene. The suspension was filtered again using the same conditions as described above.

Then, the filter cake was washed with 150 mL of toluene (displacement washing). Afterwards, the filter cake was transferred to the 0.75 liter reactor and stirred for further 60 min with 150 ml of toluene. The suspension was filtered again using the same conditions as described above.

Then, the filter cake was washed with 150 ml of toluene (displacement washing). Afterwards, the filter cake was transferred to the 0.75 liter reactor and stirred for further 60 min with 150 ml of toluene. The suspension was filtered again using the same conditions as described above. Pyripyropene was obtained at a yield of 96.4% (weight/weight) compared to the amount present in the dry biomass before extraction.

Milling and Extraction with Ethyl Benzene:
Example 1

Dry biomass obtained by paste mill drying, as described above, containing 5% residual water was submitted to milling using a Microthron MB550 apparatus, set to step 7 for 45 sec. 100 g of the milled dry biomass was submitted to a 0.75 liter-reactor stirred with a blade impeller. 200 ml of ethyl benzene were added and the suspension was stirred for 18 h at 60° C. with 250 rpm. Afterwards the suspension was filtered using a 0.5 liter glass filter (porous size 3, diameter 9.5 cm) using vacuum at 200 mbar.

The filter cake was washed again with 200 mL of ethyl benzene (displacement washing). Afterwards, the filter cake was transferred to the 0.75 liter reactor and stirred for further 60 min with 200 ml of ethyl benzene. The suspension was filtered again using the same conditions as described above.

Then, the filter cake was washed with 150 ml of ethyl benzene (displacement washing). Afterwards, the filter cake was transferred to the 0.75 liter reactor and stirred for further 60 min with 150 ml of ethyl benzene. The suspension was filtered again using the same conditions as described above.

Then, the filter cake was washed with 150 ml of ethyl benzene (displacement washing). Afterwards, the filter cake was transferred to the 0.75 liter reactor and stirred for further 60 min with 150 ml of ethyl benzene. The suspension was filtered again using the same conditions as described above. Pyripyropene was obtained at a yield of 95.3% (weight/weight) compared to the amount present in the dry biomass before extraction.

Milling and Extraction with Ethyl Benzene:

Dry biomass obtained by paste mill drying, as described above, containing 5% residual water was submitted to milling using a Microthron MB550 apparatus set to step 7 for 45 sec. 200 g of the milled dry biomass was submitted to a 0.75 liter-reactor equipped with a blade impeller. 400 ml of ethyl benzene were added and the suspension was stirred for 18 h at room temperature with 350 rpm. Afterwards the suspension was filtered using a 0.5 liter glass filter (porous size 3, diameter 9.5 cm) using vacuum at 200 mbar.

The filter cake was washed again with 400 ml of ethyl benzene (displacement washing). Afterwards, the filter cake was transferred to the 0.75 liter reactor and stirred for further 60 min with 400 ml of ethyl benzene. The suspension was filtered again using the same conditions as described above.

Then, the filter cake was washed with 300 ml of ethyl benzene (displacement washing). Afterwards, the filter cake was transferred to the 0.75l reactor and stirred for further 60 min with 300 ml of toluene. The suspension was filtered again using the same conditions as described above. Pyripyropene was obtained at a yield of 91.5% (weight/weight) compared to the amount present in the dry biomass before extraction.

Extraction with Methanol:

100 g of dry biomass obtained by paste mill drying, as described above, containing 5% residual water was submitted to a 0.75 liter-reactor equipped with a blade impeller. 200 mL of methanol were added and the suspension was stirred for 18 h at room temperature with 250 rpm. Afterwards the suspension was filtered using a 0.5 liter glass filter (porous size 3, diameter 9.5 cm) using vacuum at 200 mbar.

The filter cake was washed two times with 200 ml of methanol each (displacement washings). Afterwards, the filter cake was washed two times with 150 ml of methanol each (displacement washings). Pyripyropene was obtained at a yield of 96.9% (weight/weight) compared to the amount present in the dry biomass before extraction.

Milling and Extraction with Methanol:

The biomass obtained by paste mill drying, as described above, containing 5% residual water was submitted to milling using a Microthron MB550 apparatus set to step 7 for 45 sec. 100 g of the milled dry biomass was submitted to a 0.75 liter-reactor equipped with a blade impeller. 200 ml of methanol were added and the suspension was stirred for 18 h at room temperature with 250 rpm. Afterwards the suspension was filtered using a 0.5 liter glass filter (porous size 3, diameter 9.5 cm) using vacuum at 200 mbar.

The filter cake was washed two times with 200 ml of methanol each (displacement washings). Afterwards, the filter cake was washed two times with 150 ml of methanol each (displacement washings). Pyripyropene was obtained at a yield of 98.7% (weight/weight) compared to the amount present in the dry biomass before extraction.

Example III: Production of Dry Biomass Having 3% Residual Water Content Via Spray Drying and Extraction of Pyripyropene A with Ethyl Benzene and Methanol Biomass of *P. coprobium* produced in fed batch fermentation and suspended in culture broth was used for spray drying. The microorganism *P. coprobium* was cultivated in a 0.3 m³ fermenter with 0.2 m³ working volume. Fermentation broth (culture broth) contained 6 to 8% of biomass and 2 to 2.1% of pyripyropene A in the biomass and less than 0.1 g/L of glucose. This broth was subjected to thermal inactivation for 60 minutes at 70° C. before harvested from the fermentation vessel. Afterwards, the culture broth was homogenized using a cavitron apparatus set at a temperature of 70° C. Then, the fermentation broth was kept at 70° C. for further 30 min in a buffer tank before being spray dried.

For drying, a spry dry tower similar in construction as described by the schematic drawing in FIG. 2 has been used, with the technical features described below:

| | |
|---|---|
| Max. gasflow | 250 m³/h |
| Hole diameter aperture plate | 2 mm |
| Number aperture holes | 1.255 |
| D 1 | 1.25 m |
| H 1 | 0.31 m |
| H 2 | 1.22 m |
| H 3 | 1.36 m |
| D 2 | 66 mm |
| Nozzle type: | Nubilosa 2 compound, 2 mm |
| Depth of nozzle under aperture plate | 200 mm |
| Heating Power | 20 KW |
| Primary Separation | Cyclone (Diameter = 0.203 m, Hight = 0.5 m) |
| Filter (Filtertower) | Polyester PTFE Coating |
| Filterarea | 3.40 m2 |
| Number of tubes | 6 |
| Length of tubes | 1.10 m |
| Tube diameter | 0.16 m |

The culture broth comprising the produced biomass was fed into the spray dryer at a feed rate of 7.5 to 8.5 kg/h. Nitrogen was used as drying gas and applied with 250 m³/h and an inlet temperature of 160° C. The corresponding gas outlet temperature was 77 to 80° C. in the cyclone.

The dried biomass had a residual water content of 3% and a pyripyropene A content of 24%

This dry biomass produced in this way showed long term storage stability, because only a slight decrease of 4% pyripyropene A was observed after storage for 213 days at room temperature, as well as after storage for 242 days at 60° C.

Extraction with Ethyl Benzene:

100 g of spray dried biomass containing 3% residual water was submitted to a 0.5 liter-4-necked flask agitated with a blade impeller. 200 ml of ethyl benzene were added and the suspension was stirred for 18 h at room temperature with 530 rpm. Afterwards the suspension was filtered using a 0.5 liter glass filter (porous size 3, diameter 9 cm).

The filter cake was washed four times with 150 ml of ethyl benzene each (displacement washings). Pyripyropene was obtained at a yield of 95.6% (weight/weight) compared to the amount present in the dry biomass before extraction.

Extraction with Methanol:

100 g of spray dried biomass containing 3% residual water was submitted to a 0.5 liter-4-necked flask agitated with a blade impeller. 200 ml of methanol were added and the suspension was stirred for 18 h at room temperature with 530 rpm. Afterwards the suspension was filtered using a 0.5 liter glass filter (porous size 3, diameter 9 cm).

The filter cake was washed four times with 150 ml of methanol each (displacement washings). Pyripyropene was obtained at a yield of 98% (weight/weight) compared to the amount present in the dry biomass before extraction.

IV: Analytics and Methods

As far as not stated otherwise, the following methods have been used to determine the values presented in the Examples:

HPLC-analytics Pyripyropene

| | |
|---|---|
| Instrument: | AGILENT |
| Column: | Zorbax Eclipse XDB-C18, 1.8 µm, 50 × 4.6 mm (N° 922975.902) |

| | | |
|---|---|---|
| Pressure: | about 230 bar | |
| Wave-length of UV-detector: | 230 nm or 320 nm | |
| Temperature: | 40° C. | |

| Preparation of Solutions: | | | |
|---|---|---|---|
| Solution A: | Water (Sigma-Aldrich) with 0.1 Vol % Phosphoric acid | | |
| Organic solvent B: | Acetonitrile (Sigma-Aldrich Gradient Grade) | | |
| Gradient: | 0.0 min | 1.5 ml/min | 90% A 10% B |
| | 4.0 min | 1.5 ml/min | 70% A 30% B |
| | 11.0 min | 1.5 ml/min | 55% A 45% B |
| | 13.0 min | 1.5 ml/min | 45% A 55% B |
| | 17.0 min | 1.5 ml/min | 20% A 80% B |
| | 19.0 min | 1.5 ml/min | 0% A 100% B |
| | 20.0 min | 1.5 ml/min | 0% A 100% B |
| | 20.1 min | 1.5 ml/min | 90% A 10% B |
| | The mobile phase is automatically degassed in the HPLC apparatus. | | |
| | Post-time 3 min | | |

| | |
|---|---|
| Quantification: | External standard for pyripyropene A |
| | Peak Area in % for any unknown impurity |
| Injection Volume: | 1 µl (pyripyropene) |
| Dilution solvent: | Acetonitrile for pyripyropene |

Sample Preparation for Pyripyropene A:

Accurately weigh approximately 100 mg of sample in a 100.0 ml volumetric flask, dissolve in 40.0 ml of acetonitrile (ultrasonicate for 1 minute). If the sample is not solved in pure acetonitrile, add water and repeat sonification. Complete to volume with acetonitrile.

Standard Preparation:

A typical calibration contains 5 standard solutions:

| | |
|---|---|
| Pyripyropene: | 1. 30 mg Standard in 100 ml |
| | 2. 60 mg Standard in 100 ml |
| | 3. 90 mg Standard in 100 ml |
| | 4. 120 mg Standard in 100 ml |
| | 5. 150 mg Standard in 100 ml |

Dissolve every standard solution in acetonitril (pyripyropene A) (see sample preparation for further details). The calibration curve type is linear. The concentrations depend on the sensitivity of the detector, adjustments may be necessary.

Injection Format

4× blank/1× standard 1 to 5/sample preparation.

Retention Times

The retention times of pyripyropene A is: 7.7 min

Biomass Content Determination

Filtration of ~15 g fermentation broth; 2× washing of the filter cake with distilled water; drying of the filter cake: Halogen (IR-)—drying scales (Mettler Toledo) drying temperature 180° C. until constant weight.

Water Content Determination

1) The residual water content of the filter cake (wet biomass) was determined by calculation from the biomass content of the fermentation broth (see above) and the actual weight of the filter cake.
2) For residual water contents below ~30%: loss on drying method. Approx. 5-10 g of biomass is dried in a vacuum dryer at 80° C. and 50 mbar (20 L/h nitrogen stream) for 18 h (constant weight).
3) For residual water contents below ~10%:
   a) Halogen (IR) scales (Mettler Toledo) at 102° C., 4 h (constant weight).
   b) Karl Fischer: towards 0.1 g-0.5 g of dried biomass is added ~45 mL methanol. This suspension is stirred for a short time (~10 sec). Afterwards Karl Fischer titration is performed. This method is good for biomass of relatively small particle size due to the possibility to reach all water that is bound inside the cells. Oberschalenwaage, Magnetrührer mit Heizpilz, Glasapparatur nach
   c) Aufhäuser method: A sample of 50 g biomass is weighed into a 500 ml flask that is afterwards filled to approximately half of the volume with toluene. The water is removed by azeotropic distillation and collected in a graduated dean-stark trap until no further water is removed from the sample.

The density is assumed to be 1 g/ml:

$$\text{Water content } (\%) = \frac{\text{Water (ml)} * 100}{\text{Sample weight (g)}}$$

Glucose Determination with High Performance Liquid Chromatography:

| | |
|---|---|
| Column: | Aminex HPX-87 H, 300 * 7.8 mm (Biorad) |
| Pre-column: | Cation H |
| Temperature: | 30° C. |
| Flowrate: | 0.50 ml/min |
| Injection volume: | 5.0 µl |
| Detection: | RI-Detector |
| Duration: | 30.0 Minutes |
| Max. pressure: | 140 bar |
| Eluent: | 5 mM H2SO4 |
| Matrix: | Fermentation broth, |
| Preparation: | Sample has to be filtered at 0.22 µm cut-off. |
| Calibration: | Glucose 50 g/L in water |
| Retention time: | 10.93 min (Glucose) |

The invention claimed is:

1. A process to obtain at least one pyripyropene comprising the steps of
   a) culturing a pyripyropene producing fungus in a culture broth under culture conditions to produce a biomass comprising at least one pyripyropene,
   b) drying at least part of the biomass obtained in step a) to produce a dry biomass that contains less than 10% water,
   c) obtaining at least one pyripyropene from the dry biomass produced in step b) by reacting the dry biomass with a suitable organic solvent for a time and temperature sufficient to extract the pyripyropene from the biomass.

2. The process of claim 1, wherein the dry biomass produced in step b) is produced directly via spray drying of the culture broth comprising the biomass, or is produced via drying of wet biomass obtained from the culture broth.

3. The process of claim 2, wherein the wet biomass is obtained from the culture broth via
   a) filtration and/or centrifugation, or
   b) filtration and application of mechanical pressure, or
   c) filtration and/or centrifugation and application of mechanical pressure.

4. The process of claim 2, wherein the wet biomass
   a) has been re-suspended in a re-suspension medium,
   b) has been homogenized, c) has a glucose content of less than 5 g/l, d) has a water content between more than 15% to less than 90%, e) has a combination of at least two of a) to d).

5. The process of claim 1, wherein the dry biomass produced in step b), is produced by drying in a spray dryer, a paste mill dryer, a flash dryer, a fluid bed dryer, or a rotary dryer.

6. The process of claim 1, wherein the dry biomass produced in step b), is produced by drying in a spray dryer or a paste mill dryer.

7. The process of claim 1, wherein the dry biomass produced in step b), is stored from about 5 hours up to several years, before the pyripyropene is obtained in step c).

8. The process of claim 1, wherein the dry biomass produced in step b), contains less than 5% water.

9. The process of claim 1, wherein more than 80% of the dry biomass produced in step b), has a particle size between 0.01 mm to 5 mm.

10. The process of claim 1, wherein the dry biomass produced in step b) and used to obtain pyripyropene in step c), comprises at least 95% of the pyripyropene produced during culturing of step a).

11. The process of claim 1, wherein the pyripyropene producing fungus belongs to the genus *Penicillium, Eupenicillium* or *Aspergillus*.

12. The process of claim 1, wherein the pyripyropene producing fungus is selected from the group consisting of *Penicillium coprobium, Penicillium griseofulvum, Eupenicillium reticulosporum* and *Aspergillus fumigatus*.

13. The process of claim 1, wherein the pyripyropene producing fungus is *Penicillium coprobium*.

14. The process of claim 1, wherein the pyripyropene is obtained from the dry biomass via extraction with an organic solvent selected from the group consisting of methanol, toluene and ethyl benzene, or is a mixture of at least two of them.

15. The process of claim 1, wherein the pyripyropene is obtained from the dry biomass via extraction with an organic solvent and the solvent is separated from the biomass via a filtration step having a filter resistance below $5 \times 10^{13}$ mPas/m$^2$.

16. A process to produce at least one compound of Formula III, Formula IV or Formula V, comprising:

a) obtaining a pyripyropene via the process comprising the steps of:
  i) culturing a pyripyropene producing fungus in a culture broth under culture conditions to produce a biomass comprising at least one pyripyropene,
  ii) drying at least part of the biomass obtained in step i) to produce a dry biomass that contains less than 10% water,
  iii) obtaining at least one pyripyropene according to Formula I or Formula II from the dry biomass produced in step ii) by reacting the dry biomass with a suitable organic solvent for a time and temperature sufficient to extract the pyripyropene according to Formula I or Formula II from the biomass;

b) producing the compound of Formula III, Formula IV or Formula V from the pyripyropene of Formula I or Formula II obtained in step a).

17. The process of claim 16, wherein at least one compound of Formula III, Formula IV or Formula V, is produced from at least one compound of Formula I obtained via extraction of the dry biomass.

18. The process of claim 16, wherein a compound of Formula II is obtained via extraction of the dry biomass.

19. The process of claim 18, wherein a compound of Formula II is obtained and used to produce at least one compound of Formula III, Formula IV or Formula V.

20. The process of claim 16, wherein at least one compound of Formula III, Formula IV or Formula V is obtained or isolated after its production from a compound of Formula II.

21. The process of claim 16, wherein at least one compound of Formula III, Formula IV or Formula V is further used to produce a pest control composition.

22. The process of claim 21, wherein the pest control composition is an insecticide.

* * * * *